(12) United States Patent
Fonfe et al.

(10) Patent No.: US 10,023,531 B2
(45) Date of Patent: Jul. 17, 2018

(54) PROCESS FOR PREPARING ALKANESULFONIC ACIDS

(71) Applicants: Benjamin Fonfe, Frankfurt (DE); Harald Jakob, Hasselroth (DE); Chuanhua He, Jiangsu (CN); Andreas Doerflein, Grosskrotzenburg (DE); Sebastian Fuss, Flieden (DE)

(72) Inventors: Benjamin Fonfe, Frankfurt (DE); Harald Jakob, Hasselroth (DE); Chuanhua He, Jiangsu (CN); Andreas Doerflein, Grosskrotzenburg (DE); Sebastian Fuss, Flieden (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 15/103,784

(22) PCT Filed: Dec. 10, 2014

(86) PCT No.: PCT/EP2014/077139
§ 371 (c)(1),
(2) Date: Jun. 10, 2016

(87) PCT Pub. No.: WO2015/086645
PCT Pub. Date: Jun. 18, 2015

(65) Prior Publication Data
US 2016/0304446 A1  Oct. 20, 2016

(30) Foreign Application Priority Data

Dec. 11, 2013 (WO) ................ PCT/CN2013/089136

(51) Int. Cl.
*C07C 309/00* (2006.01)
*C07C 303/16* (2006.01)

(52) U.S. Cl.
CPC .................... *C07C 303/16* (2013.01)

(58) Field of Classification Search
CPC .................... C07C 303/16; C07C 309/04
See application file for complete search history.

(56) References Cited

U.S. PATENT DOCUMENTS

| | | | |
|---|---|---|---|
| 2,433,395 A | | 12/1947 | Proell et al. |
| 2,433,396 A | * | 12/1947 | Proell ................ C07C 303/22 562/118 |
| 2,502,618 A | | 4/1950 | Fields et al. |
| 2,697,722 A | | 12/1954 | Johnson et al. |
| 2,727,920 A | | 12/1955 | Johnson et al. |
| 4,239,696 A | | 12/1980 | Schreyer et al. |
| 6,124,497 A | | 9/2000 | Chen |

FOREIGN PATENT DOCUMENTS

| CN | 1165136 A | 11/1997 |
|---|---|---|
| CN | 101648892 A | 2/2010 |
| WO | WO 98/34914 A1 | 8/1998 |

OTHER PUBLICATIONS

International Search Report and Written Opinion dated Feb. 25, 2015, in PCT/EP2014/077139 filed Dec. 10, 2014.
Foreign Search Report and Written Opinion dated Mar. 13, 2014, in PCT/CN2013/089136 filed Dec. 11, 2013.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

The present invention relates to a process for preparing alkanesulfonic acids from dialkyl disulfides with nitric acid and oxygen.

16 Claims, 20 Drawing Sheets

PROCESS FOR PREPARING ALKANESULFONIC ACIDS

Figure 1:
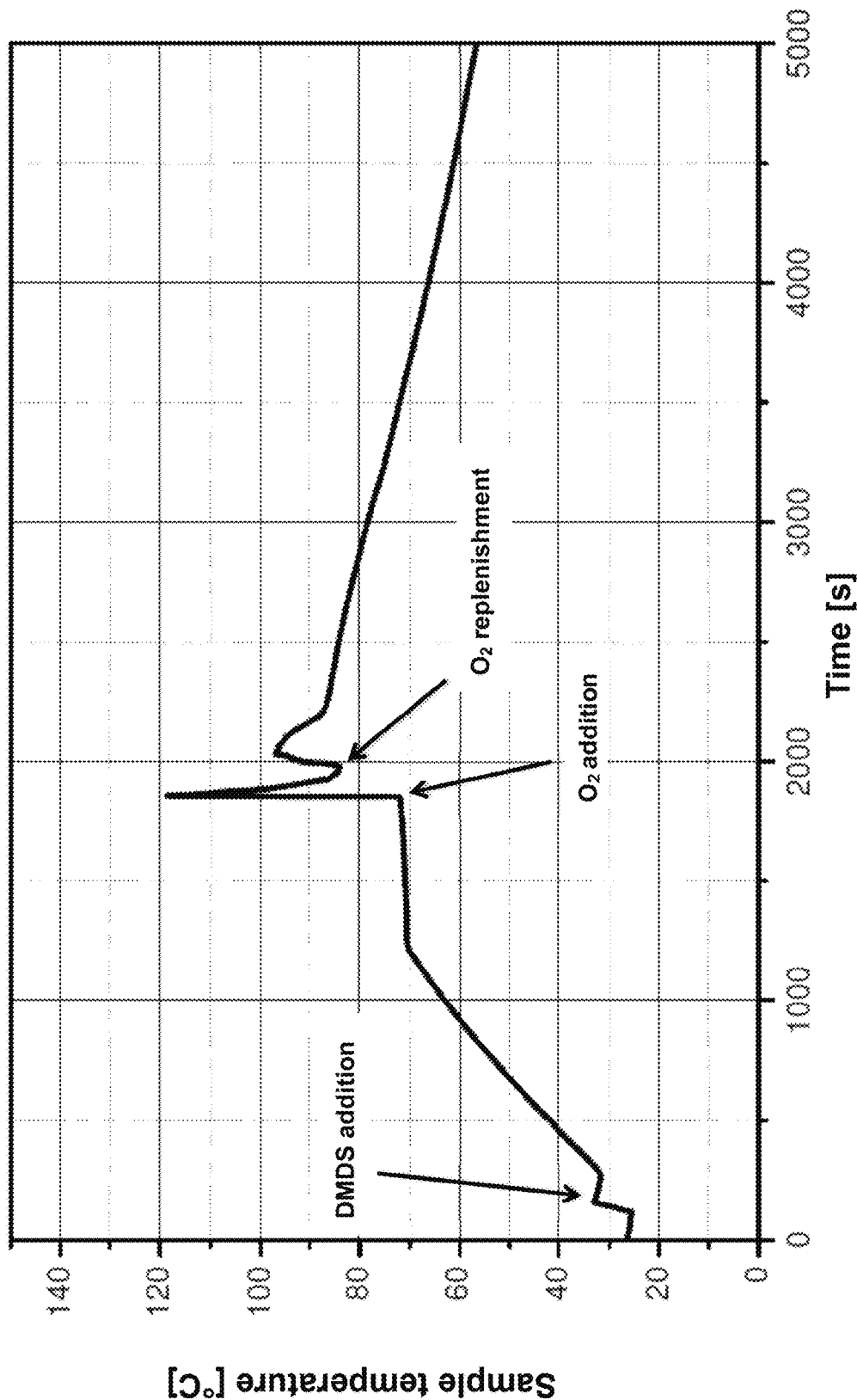

The present invention relates to a process for preparing alkanesulfonic acids from dialkyl disulfides with nitric acid and oxygen.

Alkanesulfonic acids are the organic derivatives of sulfuric acid, from which they differ structurally in the replacement of a hydroxyl group with an organic radical. The general structural formula of the alkanesulfonic acids therefore is R—SO$_3$—H, where R denotes an organic radical, such as alkyl or aryl for example. Depending on this organic radical, a distinction is made between aliphatic, aromatic or heterocyclic sulfonic acids. The free sulfonic acids are generally colourless and hygroscopic substances whose acid strength corresponds to that of the inorganic acids. Indeed, with a pK$_a$ of −5.5, trifluoromethanesulfonic acid is one of the strongest known acids and therefore belongs to the group known as the superacids. In contrast to the sulfate salts of mercury, lead and silver, the corresponding sulfonates have very good solubility in water.

The simplest representative of the alkanesulfonic acids is methanesulfonic acid, which is commonly also abbreviated to MSA, in accordance with its name as methanesulfonic acid. At the same time, by virtue of its diverse possibilities for use, methanesulfonic acid is also the most economically important alkanesulfonic acid. For example, methanesulfonic acid serves as a solvent and catalyst for a variety of organic reactions, such as alkylations, esterifications, polymerizations or heterocycle syntheses, for example. Another field of application is the formation of acid addition salts of basic pharmaceuticals with methanesulfonic acid in human medicine. In addition, methanesulfonic acid is increasingly finding use as a constituent of cleaning products, since the absence of colour and odour in this acid, allows the easy integration of methanesulfonic acid into cleaning solutions. From an industrial standpoint, the most significant are the metal salts of methanesulfonic acid, which find use as electrolytes in methanesulfonic acid electroplating baths, especially for the production of circuit boards for the electronics industry. Another new field of application for methanesulfonic acid is that of oil drilling: the petroleum-bearing strata accessed by boreholes often release the oil only to a limited extent or not at all. For enhanced release of the oil, therefore, the oil-containing rock strata are softened using methanesulfonic acid.

On the industrial scale, alkanesulfonic acids are manufactured by oxidation of alkyl mercaptans and/or dialkyl disulfides or dialkyl polysulfides.

WO 98/34914 discloses a process for oxidizing alkyl mercaptans and/or dialkyl disulfides with molecular bromine to give the corresponding alkanesulfonic acids. In this process, hydrogen bromide is initially oxidized with oxygen in the presence of catalytic amounts of nitric acid, or with nitric acid as oxidizing agent, to give molecular bromine. The oxides of nitrogen that form in this reaction are regenerated with oxygen and water to give nitric acid, which is returned to the process step of the oxidation of hydrogen bromide to molecular bromine. Thereafter, using the molecular bromine obtained in this way, the mercaptan and/or the dialkyl disulfide are or is oxidized to the corresponding alkanesulfonic acid. As a result of the use of molecular bromine, the alkanesulfonic acids prepared by the method of WO 98/34914 always contain halogen and are therefore not suitable for use in the fabrication of circuit boards. In that application, indeed, the presence of halogens must fundamentally be avoided.

It is also known to use hydrogen peroxide as oxidizing agent for the preparation of alkanesulfonic acids from alkylmercaptans or dialkyl disulfides. However, this reaction only runs without difficulties when carboxylic acids are present. It is therefore believed that the percarboxylic acid, which is formed from the carboxylic acid and the hydrogen peroxide, constitutes the real active oxidizing agent. It is particularly disadvantageous that this process results in a mixture of alkanesulfonic acids with carboxylic acids and percarboxylic acids from which the alkanesulfonic acids can often be separated in pure form only with difficulty. Thus, a cost- and energy-consuming recovery of the alkanesulfonic acids is necessary, which makes this process economically unattractive. A further cost driver is the use of hydrogen peroxide, which is a rather expensive oxidizing agent. Another disadvantage is that one mole of water is formed per one mole of reacted hydrogen peroxide and thus, considerable amounts of water are formed. However, this reaction by-product cannot be converted again to the oxidizing agent but must be separated from the desired alkanesulfonic acid by cost- and energy-consuming distillation proceedings.

U.S. Pat. No. 4,239,696 discloses an alternative process for the oxidation of alkylmercaptans and dialkyl disulfides with hydrogen peroxide. In this process alkylmercaptans or dialkyl disulfides are oxidized with hydrogen peroxide in a liquid reaction medium, which contains from 1 to 35% of an alkanesulfonic acid, based on the amount of alkylmercaptans or dialkyl disulfides, and is free of carboxylic and percarboxylic acids. The rather long reaction time of three hours and the employment of the expensive oxidizing agent hydrogen peroxide are significant disadvantages, which make this process rather unattractive from an economical point of view. More importantly, the U.S. Pat. No. 4,239,696 teaches to carry out the reaction in two steps when the process is performed as a continuous process, where the first step is carried at temperatures of up to 90° C. and the second step at temperatures between 100° C. and 110° C. However, alkanesulfonic acids such as methanesulfonic acid are corrosive at these temperatures and thus, would lead to severe corrosion phenomena, which makes this process also unattractive from a safety-related point of view.

The U.S. Pat. Nos. 2,433,395 and 4,433,396 disclose the preparation of alkanesulfonic acids by the direct oxidation of organic sulfur compounds of the general formula RS$_n$R', with R and R' being hydrocarbon radicals and n being an integer between 1 to 6, in particular dialkyl disulfides, with oxygen in the presence of catalytic amounts of nitric acid. The process of U.S. Pat. No. 2,433,395 is a one-stage oxidation of the sulfur compound at a reaction temperature of about 250° F. to 300° F. at the most, which equals a temperature range of from ca. 121° C. to ca. 148° C. By comparison, the process of U.S. Pat. No. 2,433,396 consists of a two-stage oxidation: In the first oxidation stage the sulfur compound is subjected to a temperature of from about 20° C. to about 70° C. When a concentration of sulfonic acid in the range of from 40% to about 70% is reached, a reduction of the reaction rate is observed: The reaction rate is markedly reduced, for example to about a tenth of the initial reaction rate. The reaction mixture obtained in the first oxidation stage is therefore subjected to a reaction temperature of from about 70° C. to about 150° C. in the second oxidation stage in order to increase the content of sulfonic acid in the reaction mixture. A further disadvantage is that, the product of these processes is usually a pale, reddish-brown colored product, as described in U.S. Pat. No. 2,697,722. This discoloration is at least partly attributed to color and odor bodies, which are believed to be the result of an incomplete oxidation of the respective dialkyl disulfide. It is therefore necessary to bleach the crude reaction product with concentrated nitric acid in order to remove color and odor bodies, as described for example in U.S. Pat. No. 2,697,722. Yet another disadvantage of the process of U.S. Pat. No. 2,433,395 is that the crude product of this process still contains further impurities, such as sulfur dioxide and pungent sulfoxides, whose removal requires additional cleaning steps. U.S. Pat. No. 2,433,395 also teaches to control the reaction temperature through introduction of readily evaporable liquids, such as petroleum ethers, into the mixture of the oxidation reaction. The liquids, by evaporating with a high vapour pressure, remove the heat of oxidation from the reaction mixture and so cool it. In the gas phase, however, liquids of high vapour pressure may form explosion hazard gas mixtures together with oxygen. This represents a considerable safety risk, and the process of U.S. Pat. No. 2,433,395 is therefore not suitable for industrial application.

Equally unsuited to industrial preparation of alkanesulfonic acids is the process of the U.S. Pat. No. 2,433,396. This document discloses a two-stage process for preparing alkanesulphonic acids by oxidizing a dialkyl disulphide, in solution in an alkanesulphonic acid, with oxygen and a catalytic amount of an oxide of nitrogen. The reaction of the mixtures disclosed in that document, however, is not without problems; instead, explosion hazard mixtures may be formed. Moreover, the alkanesulfonic acids prepared by that process still contain considerable amounts of nitrogen oxides, which cannot be removed from the crude alkanesulfonic acid by stripping with a gas stream or by heating. In order to obtain a clean, commercially utilizable alkanesulfonic acid, it is therefore necessary to clean the crude alkanesulfonic acid obtained by this process in a separate step, for example as disclosed in U.S. Pat. No. 2,502,618, by contacting of the alkanesulfonic acid-containing phase with an olefin that is not miscible with the acid, more particularly a monoolefin hydrocarbon having at least 8 carbon atoms. A further disadvantage of the process of U.S. Pat. No. 2,433,396 is the use of high reaction temperatures in the second oxidation stage, which favours the formation of additional odour and colour bodies as well as the formation of decomposition products. Accordingly, the processes of the U.S. Pat. Nos. 2,433,395 and 2,433,396 are not suitable for the industrial preparation of alkanesulfonic acids.

The U.S. Pat. No. 2,697,722 discloses the oxidation of hydrocarbon sulfides or polysulfides with oxygen to the corresponding alkanesulfonic acids in the presence of at least stoichiometrically amounts of nitric acid. In this way, a reduction of the reaction rate and the use of increased reaction temperatures shall be avoided. Specifically, the U.S. Pat. No. 2,697,722 teaches to perform the oxidation of the hydrocarbon sulfides or polysulfides in a liquid catalytic medium which consists of nitric acid of a concentration between about 10 and 70 percent. As a result, however, considerable amounts of water are also introduced into the reaction mixture. A further disadvantage of the process according to U.S. Pat. No. 2,697,722 is that the nitric acid is recovered by scrubbing of the nitrogen oxides containing off-gas from the oxidation process as an aqueous solution of nitrogen oxides, being essentially a dilute solution of nitric acid. This dilute nitric acid can be returned to the sulfide oxidation system and be added to the nitric acid. However, by doing so the amount of water in the oxidation system is steadily increased, which makes the separation of the alkanesulfonic acid even more cost- and energy-intensive. Alternatively, the diluted nitric acid is concentrated prior to its return to the said system. However, this alternative results in a further cost and energy investments. Yet another disadvantage of the process of U.S. Pat. No. 2,697,722 is the formation of large amounts of nitrogen oxides, which are dangerous to health and environment. For example, dinitrogen oxide, $N_2O$, is considered to be a greenhouse gas. Accordingly, cost- and energy-consuming measure must be taken in order to avoid the release of these gases to the environment and workers. The process of U.S. Pat. No. 2,697,722, therefore, is not attractive for industrial applications, neither under economical nor under safety-related aspects.

U.S. Pat. No. 2,498,318 discloses a process for oxidizing dialkyl disulfides with oxygen to alkanesulfonic acids in the presence of nitrogen oxides at temperatures of not more than 125° F., which equals 52° C., in order to prevent or at least reduce the occurrence of carbonization and corrosion in the reaction zone. These reaction conditions, however, do not allow a complete conversion of the dialkyl disulfides to the desired alkanesulfonic acids. In this process too, moreover, a pale reddish brown product is obtained, which must be bleached with concentrated nitric acid in a further step, in order to remove the colorants and odorants.

The U.S. Pat. No. 2,505,910 discloses another process for the preparation of alkanesulfonic acids by oxidizing alkyl mercaptans with oxygen in the presence of catalytic amounts of nitric acid and small amounts of water. In that process, a solution comprising an alkyl mercaptan and an oxide of nitrogen as catalyst is gassed with air. Before oxygen is absorbed in this solution, a mercaptan nitrogen oxide complex is formed. However, when the oxidation of the mercaptan in this complex begins, this occurs, according to U.S. Pat. No. 2,727,920, with almost explosive vigour. The examples of U.S. Pat. No. 2,505,910 also describe a vigorous release of $NO_2$ when the process is carried out, a phenomenon which also gives rise to severe foaming within the reactor. The process of U.S. Pat. No. 2,505,910, therefore, does not allow a simple and safe procedure and is consequently not suitable for the large-scale production of alkanesulfonic acids. In addition, the alkanesulfonic acids prepared by this process contain coloured impurities, which must be removed by treatment with concentrated nitric acid. This makes the process of U.S. Pat. No. 2,505,910 economically unattractive as well.

U.S. Pat. No. 2,727,920 discloses a process for the single-stage oxidation of alkyl mercaptans with aqueous nitric acid and oxygen to the corresponding alkanesulfonic acids. In this process, however, the aqueous nitric acid is introduced in a multi-molar excess, in other words superstoichiometrically, in relation to the mercaptan to be converted, meaning that considerable amounts of water and nitrogen oxides must be separated from the resulting alkanesulfonic acid. However, increasing the ratio of mercaptan to nitric acid is not an option, because according to U.S. Pat. No. 2,727,920 even small amounts of alkyl mercaptan react with such vigour that the metering of larger amounts of alkyl mercaptan to the nitric acid is out of the question, owing to the attendant explosion hazard. With this process, therefore, only low space-time yields are achievable. The process of U.S. Pat. No. 2,727,920, consequently, is not suited to industrial production of alkanesulfonic acids.

WO 00/31027 discloses a process for the preparation of alkanesulfonic acids by oxidizing alkyl mercaptans, dialkyl disulfides and/or dialkyl polysulfides with nitric acid at temperatures of from 50° C. to 150° C. As a result of the large fraction of nitric acid in the reaction mixture, considerable amounts of water are introduced into the reaction, and must subsequently be separated, with high energy consumption and high cost, from the desired product. Another disadvantage of this process lies in the formation of large amounts of oxides of nitrogen, which are detrimental to health and a hazard to the environment, and of which dinitrogen oxide, $N_2O$, is also rated as a greenhouse gas. In order to avoid the release of these nitrogen oxides measures must be taken, which are likewise high in cost and energy, and which therefore make the process of WO 00/31027 economically unattractive.

The published Chinese patent application CN-A 101648892 discloses the preparation of alkanesulfonic acids by oxidation of a dialkyl disulfide using air and nitric acid. In this process, nitric acid is always in excess in relation to the dialkyl disulfide to be oxidized. The decomposition of considerable amounts of nitric acid results in discoloration of the product. To remove the colour, therefore, the product mixture must be admixed with a DeNOx catalyst. Moreover, the use of large amounts of nitric acid in this process also has the disadvantage that the large quantities of water introduced must be separated off again by highly energy-consuming distillation.

It is an objective of the present invention, therefore, to provide a process for preparing alkanesulfonic acids from sulfur-containing precursor compounds that allows the inexpensive production of alkanesulfonic acids in high yields under safety-relevant aspects.

This objective is solved by oxidizing a dialkyl disulfide, introduced in the form of a solution with a concentration of not more than 20 weight percent in the corresponding alkanesulfonic acid, to give the desired alkanesulfonic acid.

The present invention accordingly provides a process for preparing alkanesulfonic acids of the formula R—$SO_3$—H, comprising the step of oxidizing a symmetrical dialkyl disulfide of the formula R—$S_2$—R, in solution in an alkanesulfonic acid, in the presence of catalytic amounts of nitric acid, with R denoting a $C_1$-$C_{12}$ alkyl radical and the alkanesulfonic acid used as solvent being identical with the alkanesulfonic acid obtained from the oxidation of the dialkyl disulfide in question, characterized in that the concentration of the dialkyl disulfide in the solution is not more than 20 weight percent (wt %), the ratio of dialkyl disulfide to nitric acid ranges from 2000:1 (mol/mol) to 1:1 (mol/mol), and the concentration of the alkanesulfonic acid used as solvent is more than 70 weight percent.

The expression "not more than 20 weight percent" is used in the context of the present invention to refer to all conceivable values from more than 0 wt.-% up to and including 20 wt.-%. The expression "not more than 20 weight percent" therefore encompasses not only the integral values 1, 2, 3, 4, 5, 6, 7, 8, 9, 10, 11, 12, 13, 14, 15, 16, 17, 18, 19 and 20 wt.-% but also all values from greater than 0 wt.-% up to and including 20 wt.-% that can be expressed by real numbers.

In the context of the present invention, the solution of the dialkyl disulfide in the relevant alkanesulfonic acid is also referred to as the reaction mixture.

The term "dialkyl disulfide" is utilized in the context of the present invention in line with the common general knowledge of the skilled person, and identifies a group of chemical compounds from the group of the organic disulfides that corresponds to the general formula $R^1$—$S_2$—$R^2$, with $R^1$ and $R^2$ each denoting a hydrocarbon radical. With the proviso that these hydrocarbon radicals are not chemically reactive under the oxidizing conditions employed in the process of the invention, and that the dialkyl disulfide in question is soluble or at least sufficiently suspendable in the alkanesulfonic acid, the process according to the present invention is not subject to any restrictions on the size or structure of the hydrocarbon radical in the dialkyl disulfide. The radicals $R^1$ and $R^2$ are linear or branched hydrocarbon radicals, preferably linear, each with a $C_1$ to $C_{12}$ alkyl radical, preferably a $C_1$ to $C_6$ alkyl radical and more particularly a $C_1$ to $C_4$ alkyl radical, optionally substituted by radicals which are not reactive under conditions for oxidation reactions. $R^1$ and $R^2$ are preferably selected from the group consisting of methyl, ethyl, n-propyl, isopropyl, n-butyl, isobutyl and tert-butyl. Since the dialkyl disulfide used in accordance with the invention is symmetrical, the radicals $R^1$ and $R^2$ are identical.

The ratio of dialkyl disulfide to nitric acid of 2000:1 (mol/mol) to 1:1 (mol/mol) encompasses all ratios which can be expressed by integral and real numbers, from inclusive of 2000:1 (mol/mol) to inclusive of 1:1 (mol/mol). This ratio expressly encompasses but is not limited to the ratios 2000:1 (mol/mol), 1000:1 (mol/mol), 500:1 (mol/mol), 200:1 (mol/mol), 100:1 (mol/mol), 80:1 (mol/mol), 60:1 (mol/mol), 40:1 (mol/mol), 30:1 (mol/mol), 20:1 (mol/mol), 10:1 (mol/mol), 2:1 (mol/mol) and 1:1 (mol/mol).

In the context of the present invention, the stated concentration figures denote the concentrations of specific components in the reaction mixture at the start of the reaction. For example, the figure for a dialkyl disulfide concentration relates to the concentration which comes about after the dialkyl disulfide has been fed into the reactor and after it has subsequently mixed with the alkanesulfonic acid, with the amounts of the other compounds present being negligible. Correspondingly, the figure for an alkanesulfonic acid concentration relates to the concentration which comes about after the alkanesulfonic acid has been fed into the reactor and after its subsequent mixing with the dialkyl disulfide, with the amounts of the other compounds present being negligible.

If the process according to the present invention is carried out in batch operation, the initial concentration of the dialkyl disulfide in the reaction mixture is not more than 20 wt.-%, and also decreases continuously over the entire course of the reaction. The initial concentration of the alkanesulfonic acid in the process of the invention is then 80 wt.-% and, because of the continual formation of alkanesulfonic acid, increases continuously over the course of the reaction. In continuous operation, in contrast, there is permanently a concentration of the dialkyl disulfide of 20 wt.-% at most.

By these means it is ensured that the oxidation of a dialkyl disulfide to the corresponding alkanesulfonic acid can be carried out safely and with no explosion propensity even on the industrial scale. The fact, indeed, that the oxidation takes place in a solution with more than 70 weight percent of an alkanesulfonic acid ensures that the liberated reaction heat, which is particularly high at the start of the reaction, is absorbed by a high-boiling solvent (for methanesulfonic acid, the boiling point is about 167° C. at 13 hPa). The advantage of this is that the oxidation of dialkyl disulfides to alkanesulfonic acids proceeds smoothly rather than explosively in the process according to the present invention. Moreover, when the process according to the present invention is performed in a batch reactor, there is, as reaction time progresses, a reduction in the liberated reaction heat, owing to the continuously decreasing concentration of dialkyl disulfide.

The use of an alkanesulfonic acid as high-boiling solvent has the additional safety advantage that the tendency to form gas mixtures from organic compounds and oxygen is avoided or at least reduced to an extent such that there is no risk of explosion.

If, on the other hand, the dialkyl disulfide concentration exceeds 20 wt.-% as is the case in known processes, the heat of reaction that is released can no longer be controlled to the level required for an industrial process.

The fact that the process of the present invention uses an alkanesulfonic acid as solvent that is also the target product of this process at the same time removes the need—which exists in the known preparation processes for alkanesulfonic acids—to separate the solvent from the desired product. Consequently, in the process of the invention, the distillative purification of the crude product is significantly less costly and complex, and this entails correspondingly lower capital costs and operating costs.

According to the view put forward in the literature, the oxidation of alkanesulfonic acids from dialkyl disulfides proceeds via the intermediates of an S-alkylthioalkane sulfoxide R—S—SO—R, followed by an S-alkyl thioalkanethiosulfonate R—S—$SO_2$—R, an S-alkyl sulfoxide alkanethiosulfonate R—SO—$SO_2$—R and a dialkyl disulfone R—$SO_2$—$SO_2$—R, with the latter being finally hydrolysed to the desired alkanesulfonic acid. The combined use of an alkanesulfonic acid as solvent and catalytic amounts of nitric acid in the process according to the present invention has the advantage over prior-art processes that only the quantities of water, which are required to form the desired alkanesulfonic acid, need be introduced into the reaction. This permits the preparation of a substantially anhydrous alkanesulfonic acid. The concluding distillative purification of the "crude" alkanesulfonic acid therefore serves primarily only for the purpose of relieving the desired alkanesulfonic acid of impurities in the trace range and of oxides of nitrogen resulting from the thermal decomposition of the nitric acid. This distillation of the "crude" alkanesulfonic acid therefore requires not only less—and less complex—apparatus, but also less energy, and the capital costs and energy costs of the process of the invention are therefore significantly lower than in the case of the processes known from the prior art.

The process of the present invention is especially suitable for the preparation of methanesulfonic acid. By means of the process of the invention, indeed, methanesulfonic acid can be obtained with a purity of at least 95%, preferably at least 97% and more preferably at least 99%. The significantly reduced water content results in fewer disruptions, particularly when the methanesulfonic acid is employed as catalyst in chemical reactions.

In one embodiment of the present invention, therefore, the dialkyl disulfide which is reacted to the corresponding alkanesulfonic acid is dimethyl disulfide, and the alkanesulfonic acid obtained is methanesulfonic acid.

In accordance with the invention, the process according to the present invention can be carried out even with a comparatively low ratio of dialkyl disulfide to nitric acid of 1000:1 (mol/mol) and even 2000:1 (mol/mol) and also at any desired ratios between inclusive of 1000:1 (mol/mol) and inclusive of 2000:1 (mol/mol). By increasing the nitric acid concentration to a ratio of dialkyl disulfide to nitric acid of 500:1 (mol/mol), the predominant fraction of the dialkyl disulfide is reacted to the alkanesulfonic acid within just 90 minutes.

In one embodiment of the present invention, the ratio of dialkyl disulfide to nitric acid is therefore 500:1 (mol/mol) to 1:1 (mol/mol).

Increasing the nitric acid concentration further, to a ratio of dialkyl disulfide to nitric acid of 100:1 (mol/mol), even allows virtually complete conversion of the dialkyl disulfide to the alkanesulfonic acid within 60 minutes. As a result of further increase in the nitric acid concentration, to a ratio of dialkyl disulfide to nitric acid of 10:1 (mol/mol), dialkyl disulfides are in fact oxidized almost completely to the corresponding alkanesulfonic acid in just half an hour.

Preferably, the ratio of dialkyl disulfide to nitric acid is therefore 100:1 (mol/mol) to 1:1 (mol/mol).

The ratio of dialkyl disulfide to nitric acid is preferably 80:1 (mol/mol) to 1:1 (mol/mol), 60:1 (mol/mol) to 1:1 (mol/mol), 40:1 (mol/mol) to 1:1 (mol/mol), 20:1 (mol/mol) to 1:1 (mol/mol), or 10:1 (mol/mol) to 1:1 (mol/mol).

Alternatively, it is advantageous that the ratio of dialkyl disulfide to nitric acid is always larger than 1:1 because the amount of nitric acid can thus be significantly reduced, which further improves the cost efficiency of the process according to the present invention. Since the nitric acid employed in the process is always regenerated under the reaction conditions of that process, the use of smaller amounts of nitric acid has no negative effects on the yield and the selectivity for the formation of the alkanesulfonic acid. Further, there is no significant increase in reaction time when the ratio of dialkyldisulfide to nitric acid is equal to or larger than 2:1 (mol/mol).

The ratio of dialkyl disulfide to nitric acid is therefore preferably 500:1 (mol/mol) to 2:1 (mol/mol), 200:1 (mol/mol) to 2:1 (mol/mol), 100:1 (mol/mol) to 2:1 (mol/mol), 80:1 (mol/mol), 60:1 (mol/mol) to 2:1 (mol/mol), 40:1 (mol/mol) to 2:1 (mol/mol), 20:1 (mol/mol) to 2:1 (mol/mol), or (10:1 (mol/mol).

In an alternative embodiment of the present invention, the ratio of dialkyl disulfide to nitric acid is therefore 500:1 (mol/mol) to 2:1 (mol/mol).

The process of the present invention allows the preparation of alkanesulfonic acids from the corresponding dialkyl disulfides with yields of more than 90% from safety aspects with a maximum concentration of the dialkyl disulfide in the alkanesulfonic acid of not more than 20 weight percent. From safety aspects, however, it is even more favourable for the process of the invention to be carried out with a concentration of not more than about 10 weight percent of the dialkyl disulfide in the alkanesulfonic acid. The reason is that in that case the development both of the temperature and of the pressure during the oxidation of the dialkyl disulfide are lower than if the concentration of the dialkyl disulfide is more than 10 weight percent or even up to 20 weight percent. This permits even more effective control of temperature when implementing the process of the invention.

In a further embodiment of the present invention, the concentration of the dialkyl disulfide in the alkanesulfonic acid is up to about 10 weight percent.

The concentration of the dialkyl disulfide in the alkanesulfonic acid is preferably about 1 to about 6 weight percent, more preferably about 2 to about 6 weight percent and more particularly about 4 to about 6 weight percent.

The expression "about" in connection with weight percent is used in the context of the present invention to refer not only to the figure explicitly given but also to those figures which deviate by +/−10% from the figures explicitly given. The term "about 10 weight percent", therefore, encompasses not only the integral figures of 9, 10 and 11 weight percent but also all figures which can be expressed by real numbers and lie between inclusive of 9 and inclusive of 11 weight percent. The term "about 2 weight percent" encompasses not only the integral figure of 2 but also all values which can be expressed by real numbers and which lie between inclusive of 10% less than 2 wt.-% up to and including 10% greater than 2 wt.-%. The term "about 4 to about 6 weight percent" encompasses the integral figures of 4, 5 and 6 weight percent and also all figures which can be expressed by real numbers and lie between inclusive of 10% less than 4 wt.-% up to and inclusive of 10% greater than 6 wt.-%.

With regard to the temperature regime, it has been found that in the oxidation of dialkyl disulfides to the corresponding alkanesulfonic acids, elemental sulfur is precipitated if the temperatures in the process are more than 90° C. This is attributed to a scarcity of oxygen in the reaction mixture at high temperatures during the oxidation of the dialkyl disulfides: it is thought that in the event of an oxygen deficit in the reaction mixture, the sulfur atoms in the dialkyl disulfide are not fully oxidized to sulfur with a positive formal charge. In other words: it is thought that the dialkyl disulfide is not completely oxidized to an S-alkylthioalkane sulfoxide R—S—SO—R, to an S-alkylthio alkanethiosulfonate R—S—SO$_2$—R, to an S-alkyl sulfoxide alkanethiosulfonate R—SO—SO$_2$—R or to a dialkyl disulfone R—SO$_2$—SO$_2$—R. It is additionally thought that the oxidation stops at sulfur with the formal charge 0, which is said to be accompanied by destruction of the organic compound, to which the observed precipitation of elemental sulfur is attributed. Sulfur precipitates must be prevented in the industrial production of alkanesulfonic acid, since the precipitated sulfur is detrimental to the quality of the product, reduces the yield of the desired alkanesulfonic acid, and may lead to failures because of clogged pipelines, pumps, columns, etc. Reaction temperatures of permanently above 90° C. must therefore be avoided.

A reaction temperature of not more than 90° C. in the process according to the present invention has the advantage, moreover, that no explosion hazard gas mixtures with oxygen are formed. The reason is that the boiling points of alkanesulfonic acids are well above 90° C.; for example, the boiling temperature of methanesulfonic acid, the simplest alkanesulfonic acid, is 167° C. at 13 hPa. The boiling point of dimethyl disulfide as well, the simplest representative of the dialkyl disulfides, is 110° C. and hence above the maximum temperature in the process of the invention. The ignition temperature of dimethyl disulfide is significantly higher: it is 370° C. in air under 1 atm.

In a further embodiment of the present invention, therefore, the process is carried out at temperatures of not more than 90° C.

The process according to the present invention is preferably carried out at a temperature of about 30° C. to 90° C. The reason is that, irrespective of the ratio of the dialkyl disulfide to the nitric acid in the reaction mixture, these temperatures permit virtually complete oxidation of the dialkyl disulfide to the alkanesulfonic acid. The expression "about 30° C." is used in the context of the present invention such as to also encompass values which deviate for a short time, in other words for a time period which is negligible in comparison to the reaction time, by up to −5° C. from 30° C.

At low temperatures, however, owing to the relatively low supply of energy, the oxidation reaction is not completed until a correspondingly longer reaction time has elapsed. For instance, at a reaction temperature of 30° C. or 40° C., the oxidation of dimethyl disulfide to methanesulfonic acid requires approximately three or four hours, in order to achieve virtually complete conversion of the dimethyl disulfide. Implementing the same reaction at a temperature of 70° C. or 90° C. leads to the virtually complete conversion of the dialkyl disulfide within a period just of well below an hour.

In a preferred embodiment of the process according to the present invention, the process is carried out at a temperature of about 70° C. to 90° C.

The expression "about 70° C." is used in the context of the present invention such as to also encompass values which deviate for a short time, in other words for a time period which is negligible in comparison to the reaction time, by up to −5° C. from 70° C.

In the process according to the present invention, the concentration of the dialkyl disulfide to be oxidized is not more than 20 wt.-%. The weight fraction of the nitric acid in the reaction mixture can be approximately disregarded, since in the process of the invention it is used only sub-stoichiometrically relative to the dialkyl disulfide.

In the context of the present invention, the term "stoichiometric", in relation to the ratio of nitric acid to dialkyl disulfide, is used to refer to a ratio of nitric acid to dialkyl disulfide of 1:1. Correspondingly, in the context of the present invention, the term "sub-stoichiometric", in relation to the ratio of nitric acid to dialkyl disulfide, is used to refer to all ratios of nitric acid to dialkyl disulfide that lie below a ratio of nitric acid to dialkyl disulfide of 1:1—for example, a ratio of dialkyl disulfide to nitric acid of 80:1 (mol/mol), 60:1 (mol/mol), 40:1 (mol/mol), 20:1 (mol/mol) or 10:1 (mol/mol).

In the process of the present invention, therefore, the reaction mixture may comprise 80 wt.-% of alkanesulfonic acid or more. In addition, however, it is also possible for further components, which act as solvents and are inert under the oxidizing conditions, to be present in the reaction mixture. Supplementary inert components are those which can be separated by distillation from the desired alkanesulfonic acid and that have a low vapour pressure, meaning that they do not cause explosive mixtures in the gas phase. Exemplary inert components, recited without limitation, are sulfoxide and dimethyl formamide. The fraction of the alkanesulfonic acid in the reaction mixture is preferably as high as possible, since the alkanesulfonic acid used as solvent in the reaction mixture is identical with the oxidation product and therefore, with good yields, need not be removed distillatively from the product mixture.

In a further embodiment of the present invention, the concentration of the alkane sulfonic acid used as solvent is therefore at least 80 wt.-%.

In the context of the present invention, the expression "at least 80 wt.-%" is used in such a way that it encompasses all figures from inclusive of 80 weight percent to less than 100 wt.-%. The expression "80 wt.-%" therefore encompasses the integral figures 80, 81, 82, 83, 84, 85, 86, 87, 88, 89, 90, 91, 92, 93, 94, 95, 96, 97, 98 and 99 wt.-% and also all conceivable values from inclusive of 80 to less than 100 wt.-% that can be expressed using real numbers.

The concentration of the alkanesulfonic acid in the process according to the present invention is preferably at least about 90 weight percent, more particularly at least about 92 weight percent, and more preferably the concentration of the alkanesulfonic acid used ranges from about 92 to about 96 weight percent. The expressions "about 90, about 92 and about 96 weight percent" are used in the context of the present invention to refer also to deviations of ±2 weight percent from the respective figure explicitly stated. The expression "at least about 90 weight percent" therefore encompasses all figures from inclusive of 88 weight percent to less than 100 weight percent. These are, expressly, the integral figures 88, 89, 90, 91, 92, 93, 94, 95, 96, 97, 98 and 99 weight percent and also all conceivable values from inclusive of 88 to less than 100 weight percent that can be expressed using real numbers. The expression "at least about 92 weight percent" encompasses all figures from inclusive of 90 weight percent to less than 100 weight percent: these are, expressly, the integral figures 90, 91, 92, 93, 94, 95, 96, 97, 98 and 99 weight percent and also all conceivable values from inclusive of 90 to less than 100 weight percent that can be expressed using real numbers. Correspondingly, the expression "about 92 to about 96 weight percent" encompasses all figures from inclusive of 90 to inclusive of 98 weight percent: these are, expressly, the integral figures 90, 91, 92, 93, 94, 95, 96, 97 and 98 weight percent and also all conceivable values from inclusive of 90 to inclusive of 98 weight percent that can be expressed using real numbers.

In a preferred embodiment of the present invention, therefore, the concentration of the alkanesulfonic acid used as solvent is at least about 90 weight percent.

The process of the present invention is not fundamentally subject to any restrictions on the oxidizing agent, provided that it remains ensured that the oxidation can be carried out safely. In accordance with the invention, oxygen, both in free form and in bound form, is a suitable oxidizing agent in the process of the invention. In the context of the present invention, the term "oxygen in free form" is used in accordance with the common general knowledge of the skilled person and refers to oxygen which is not, through covalent bonds, part of an organic or inorganic compound. Oxygen in free form is, for example, molecular oxygen $O_2$, ozone $O_3$ or an oxygen radical. In accordance with this understanding, therefore, an oxygen molecule or an oxygen radical that is part of a complex or is present in coordinated form, for example, is also interpreted as oxygen in free form. Oxygen in free form used in the process of the invention may therefore include pure oxygen or an oxygen-enriched gas stream, such as oxygen-enriched air or a mixture of pure oxygen and a gas which is not reactive under the oxidizing conditions, referred to as an inert gas, nitrogen or argon, for example. Conversely, the term "oxygen in bound form" refers to any oxygen which, as a result of at least one covalent bond, is part of an organic or inorganic compound. These compounds with oxygen in bound form are ultimately used to transfer oxygen atoms onto the sulfur atoms present in the dialkyl disulfide, in order to oxidize them from the formal oxidation state of −1 in the dialkyl disulfide (in steps) to the oxidation state of +3 in the dialkyl disulfone. Alternatively, in the context of the present invention, it is also possible to make simultaneous use of oxygen in free form and of oxygen in bound form to oxidize the dialkyl disulfide.

In one embodiment of the present invention, therefore, for the oxidation, air, a gas stream enriched with oxygen in free form, and/or pure oxygen in free form, is fed in.

Preference for the oxidation is given to using oxygen in free form or a gas stream enriched with oxygen in free form. The reason is that, as a result of the molecular oxygen and also the water present in the reaction mixture, the oxides of nitrogen which have formed as a result both of the oxidation reaction and of thermal decomposition are regenerated to give the nitric acid again. During the implementation of the process of the invention with nitric acid as oxidizing agent, this regeneration is an automatic and always accompanying reaction. Accordingly, in the same reactor in which the alkanesulfonic acid and the nitrogen oxides are formed, also the regeneration of the nitrogen oxides with oxygen and water to nitric acid proceeds. An advantage of this is that there is preferably no need for continuous addition of nitric acid in the process of the invention.

If, however, the oxides of nitrogen are not fully regenerated to the nitric acid, and there is a consequent loss of nitric acid, such loss can be compensated by addition of fresh nitric acid. This supplementation of not regenerated and hence lost nitric acid may take place either sporadically or continuously, depending on the particular amounts required.

Oxidation of the dialkyl disulfide by means of a gas stream enriched with oxygen in free form has the advantage that a gas stream which is more cost-effective, relatively, than pure oxygen is fed into the reaction. Furthermore, in line with the course of the oxidation reaction, the amount of oxygen in the gas stream to be fed in can be adjusted at will. In the simplest case, this gas stream is air containing more than the 20.942 vol.-% (volume percent) of oxygen commonly in air.

By feeding a gas stream with more than 21 vol.-% of oxygen in free form into the reaction mixture, it is ensured both that there is very substantially complete oxidation of the dialkyl disulfide to the corresponding alkanesulfonic acid and that there is regeneration of the oxides of nitrogen $NO_x$ to the nitric acid.

In a preferred embodiment of the present invention, therefore, a gas stream containing oxygen in free form, with a free-form oxygen content of more than 21 vol.-%, is fed in for the oxidation.

In the context of the present invention, the expression "more than 21 vol.-% of oxygen in free form" refers to all figures from greater than 21 vol.-% to inclusive of 100 vol.-% that can be expressed by integral and by real numbers. In the limiting case, the gas stream with a free-form oxygen content of more than 21 vol.-% is pure oxygen in free form, preferably molecular oxygen $O_2$.

The process of the present invention is not fundamentally subject to any restrictions on the pressure at which it is performed. The setting of the pressure in the process of the present invention is accomplished typically by way of a gas stream containing oxygen in free form that is fed into the reaction mixture. In accordance with the invention this may be air, a gas stream enriched with oxygen in free form, more particularly a gas stream containing more than 21 vol.-% of oxygen in free form, or pure oxygen in free form.

The process of the present invention is not fundamentally subject to any restrictions on the pressure. The upper pressure limit is determined by the pressure resistance of the reactor employed. Since high or very high pressures necessitate complicated and costly reactors, the process of the present invention is preferably operated at pressures of not more than 100 bara. In practice, moreover, it has emerged that a pressure of 20 bara leads neither to an increase in the yield nor to more rapid completion of the reaction. In the context of the present invention, the expression "bara" is synonymous with "bar absolute" and is used as a unit for the absolute pressure. In accordance with the common general knowledge of the skilled person, the absolute pressure is measured without taking account of the prevailing air pressure, in other words absolutely relative to the zero pressure in empty space. Preferably, however, the process of the present invention is carried out at superatmospheric pressure. In the context of the present invention, the expression "superatmospheric pressure" is used in such a way that it encompasses all pressures in the range of more than 1 bar that can be expressed using integral or real numbers.

In one embodiment of the present invention, therefore, the process is carried out at a pressure of more than 1 bara to 20 bara.

The pressure of about 20 bara is used in the context of the present invention in such a way that it also encompasses deviations of +/−10% from the figure explicitly stated. The expression "about 20 bara" therefore also encompasses all integral figures from inclusive of 18 bara to inclusive of 22 bara, explicitly the figures 18, 19, 20, 21 and 22 bara, and also all figures that can be expressed using real numbers, from inclusive of 18 bara to inclusive of 22 bara.

The pressures to which the reaction mixture is subjected are advantageously selected such that they lead to an increase in the product yields. On the basis of a yield for the formation of methanesulfonic acid of roughly over 96% at a pressure of more than 2 bara, such as at 3 bar, for example, a staged increase in pressure by 3 bara in each case leads, given constant temperature, to an increase in the yield to up to more than 99%.

In a preferred embodiment of the present invention, therefore, the process is carried out at a pressure of more than 2 bara to about 15 bara.

The pressure of about 15 bara is used in the context of the present invention in such a way that it also encompasses deviations of +/−2 bara from the figure explicitly stated. The expression "about 15 bara" therefore encompasses all integral figures from inclusive of 13 bara to inclusive of 17 bara, explicitly the figures 13, 14, 15, 16 and 17 bara, and also all figures that can be expressed using real numbers, from inclusive of 13 bara to inclusive of 17 bara.

A reactor for the oxidation reaction is preferably preceded by a mixer, in order to improve the homogeneity of the reaction mixture. This additional mixer prevents or reduces a non-optimum homogeneity or separation of the reaction mixture into different phases. Improved homogeneity on the part of the reaction mixture hence also contributes to improved kinetics in the reaction, with consequences of an improved yield of the desired alkanesulfonic acid. The reaction mixture can be homogenized in a static or a dynamic mixer. A static mixer in the sense of the present invention is a mixer in which optimum mixing of the fluids takes place not by moving components such as a stirrer or a screw, but instead only by a particular, constructionally imposed flow movement of the fluids to be mixed. A dynamic mixer in the sense of the present invention, in contrast, is a mixer in which optimum mixing of the fluids does take place as a result of moving components. In the context of the present invention, therefore, a dynamic mixer is understood to include a continuously operated stirred tank in which there is no oxidation reaction, since, for example, the energy required to initiate or to maintain the reaction, or the catalytically active nitric acid, are not supplied.

The homogenizing is preferably carried out in a static mixer. The reason is that in this way there is no need for the fault-susceptible and possibly maintenance-intensive moving components of a dynamic mixer. The at least one reactor for the oxidation reaction is therefore preferably preceded by a static mixer.

Further factors which lead to an increase in the yield of alkanesulfonic acid are a fine division and also a high residence time of oxygen in the reaction mixture. This is achieved, for example, by feeding in oxygen using what is called a jet nozzle or using a perforated plate, by means of suitable stirring elements in the reactor, or by carrying out the reaction in a long and slim, continuously operated stirred tank reactor.

In the process of the invention, furthermore, one or more solubilizers may be used in order to ensure improved homogeneity of the reaction mixture. In the context of the present invention, the term "solubilizer" is used in accordance with the common general knowledge of the skilled person to identify a compound which contributes to the dissolution of a compound with low solubility in a solvent. Basically, all compounds are suitable as solubilizers for the process of the invention, provided that they enable the dissolution of a dialkyl disulfide in the corresponding alkanesulfonic acid and themselves, under the conditions for the oxidation of the dialkyl disulfide to the alkanesulfonic acid, react neither with the dialkyl disulfide nor with any intermediate or with the desired end product. The selection of the at least one solubilizer is governed by the absolute requirement for easy separability from the desired alkanesulfonic acid. If the boiling point of the desired alkanesulfonic acid differs sufficiently from the boiling point of the solubilizer or boiling points of the solubilizers, the alkanesulfonic acid can be separated from the at least one solubilizer by distillation. This may entail additional capital costs, operating costs and energy costs. If the boiling points of the alkanesulfonic acid and of the at least one solubilizer are not sufficiently different from one another, or if the distillative separation of the at least one solubilizer has an adverse effect on the desired alkanesulfonic acid, alternatively, it is preferred not to separate off the at least one solubilizer by distillation. The latter alternative causes no problems if the fact, that the at least one solubilizer remains in the alkanesulfonic acid, has no adverse effect on the alkanesulfonic acid and on its subsequent end uses.

In a further embodiment of the present invention, therefore, a solubilizer between the dialkyl disulfide and the alkanesulfonic acid is used.

The use of alkanesulfonic acid S-alkyl ester of the formula R—SO$_2$—S—R in the process of the invention produces effective solubilization between the dialkyl disulfide and the corresponding alkanesulfonic acid. The advantage of this specific solubilizer over others is that it is formed as an intermediate in the oxidation of dialkyl disulfides to alkanesulfonic acids and is therefore able, under the reaction conditions of the process according to the present invention, to undergo further reaction to the desired oxidation product. Generally speaking, the alkanesulfonic acid S-alkyl ester that is formed during the process of the invention undergoes almost complete further reaction to the alkanesulfonic acid within a maximum of 2 hours. Therefore, the radical R of the alkanesulfonic acid S-alkyl ester is identical with the radical R of the alkanesulfonic acid obtained by the process of the present invention, and thus, it has the same meaning as defined above in context with the alkanesulfonic acid. For the preparation of methanesulfonic acid from dimethyl disulfide, therefore, a particularly preferred solubilizer is methanesulfonic acid S-methyl ester (MMTS). Particularly at concentrations of more than about 7 weight percent of dimethyl disulfide in methanesulfonic acid, MMTS has proved to be a particularly good solubilizer.

In a preferred embodiment of the present invention, therefore, alkanesulfonic acid S-alkyl ester of the formula R—SO$_2$—S—R is used as solubilizer between the dialkyl disulfide and the alkanesulfonic acid, with the alkyl radicals R of the alkanesulfonic acid S-alkyl ester being identical with the alkyl radicals R of the dialkyl disulfide to be converted and with the alkyl radical R of the alkanesulfonic acid.

With particular preference, the reaction mixture comprising dialkyl disulfide is present in one phase both before and during the oxidation of the dialkyl disulfide. This is achieved more particularly through the combination of a static mixer, upstream of the at least one reactor for the oxidation reaction, with alkanesulfonic acid S-alkyl ester as solubilizer between dialkyl disulfide and alkanesulfonic acid in the oxidation reaction.

Basically, the process of the present invention is not subject to any restrictions regarding the type of reactor used for performing the process. Therefore, the process can be performed either discontinuously in a batch reactor or continuously in a tubular flow reactor or in a continuously stirred tank reactor. Preference is given to the use of a rector, which also to perform the process of the present invention in a continuous way.

As far as the number of reactors is concerned, the process of the present invention is not in principle subject to any restrictions. The process of the invention may therefore take place in a single reactor, such as in a stirred tank reactor, for example, or in two or more reactors, such as in a combination of a main reactor with a finisher reactor or after-reactor, for example. By way of example, a continuously operated stirred tank reactor, as the main reactor, in which the greatest amount of the dialkyl disulfide is reacted, may be combined with a tubular flow reactor as finisher reactor or after-reactor, which serves for completing the oxidation reaction. To achieve complete conversion of the dialkyl disulfide, this combination needs only comparatively small reactor volumes. If, conversely, the process of the present invention is carried out in a single reactor, preferably a continuously operated stirred tank, complete conversion of the dialkyl disulfide requires a significantly greater reactor volume.

Preferably, therefore, the process of the present invention is carried out in a combination of a main reactor with an after-reactor, more particularly in a combination of a continuously operated stirred tank reactor with a tubular flow reactor.

If the process of the invention is operated in a reactor combination of a continuously operated stirred tank as main reactor with a tubular flow reactor as after-reactor, then preferably nitric acid and/or oxygen are or is fed additionally into the tubular flow reactor in order to ensure virtually complete oxidation of the remaining fraction of the dialkyl disulfide to the alkanesulfonic acid.

The internal volume of the at least one reactor in which the reaction is carried out is preferably filled completely with the reaction mixture comprising at least dialkyl disulfide and alkanesulfonic acid. If a gas phase forms over the liquid phase or the actual reaction mixture, the volume of this gas phase is very small, and so the consequences of a potential explosion are unobjectionable. It is possible, for example, for individual gas bubbles to ascend to a region over the reaction mixture. Since, however, the volume of these gas bubbles is negligibly small as compared with the reaction mixture or with the overall reactor volume, any explosion within the gas bubbles is not noticeable.

When the process of the invention is carried out in two or more reactors, as well, the internal volume at least of the first of a number of reactors should to be filled completely with the reaction mixture. The reason is that the concentration of the dialkyl disulfide, which could form an explosion hazard mixture with oxygen in free form, is the highest in the first of a number of reactors. The tendency for explosion hazard mixtures to form is therefore also the highest in the first of a number of reactors. For this reason, preferably, the internal volume at least of the first of a number of reactors is filled completely with the reaction mixture comprising at least dialkyl disulfide and alkanesulfonic acid.

After the oxidation of the dialkyl disulfide to the corresponding alkanesulfonic acid, the product mixture obtained from this conversion is subjected to distillative purification. The distillative purification preferably subdivides into a first and a downstream, second distillation, the first distillation removing the low boilers and the second distillation the high boilers from the alkanesulfonic acid. In the simplest case, this distillative purification is carried out in two distillation columns. Alternatively this distillative purification may also take place in two thermally coupled distillation columns or in what is called a dividing wall column. The process of the invention preferably therefore also encompasses the purification of the alkanesulfonic acid obtained from the process of the invention, in a dividing wall column or in at least two distillation columns, preferably in at least two thermally coupled distillation columns.

The present invention is further described by the following items:

1. Process for preparing alkanesulfonic acids of the formula $R-SO_3-H$, comprising the step of oxidizing a symmetrical dialkyl disulfide of the formula $R-S_2-R$, in solution in an alkanesulfonic acid, in the presence of catalytic amounts of nitric acid, with R denoting a $C_1$-$C_{12}$ alkyl radical and the alkanesulfonic acid used as solvent being identical with the alkanesulfonic acid obtained from the oxidation of the dialkyl disulfide in question, characterized in that the concentration of the dialkyl disulfide in the solution is not more than 20 weight percent, the ratio of dialkyl disulfide to nitric acid ranges from 2000:1 (mol/mol) to 1:1 (mol/mol), and the concentration of the alkanesulfonic acid used as solvent is more than 70 weight percent.
2. Process according to item 1, wherein the dialkyl disulfide is dimethyl disulfide and the alkanesulfonic acid is methanesulfonic acid.
3. Process according to item 1 or 2, wherein the ratio of dialkyl disulfide to nitric acid ranges from 500:1 (mol/mol) to 1:1 (mol/mol).
4. Process according to item 1 or 2, wherein the ratio of dialkyl disulfide to nitric acid ranges from 500:1 (mol/mol) to 2:1 (mol/mol).
5. Process according to any one of items 1 to 4, wherein the concentration of the dialkyl disulfide in the alkanesulfonic acid is up to about 10 weight percent.
6. Process according to any one of items 1 to 5, wherein the process is carried out at temperatures of not more than about 90° C.
7. Process according to item 6, wherein the process is carried out at temperatures of about 70° C. to about 90° C.
8. Process according to any one of items 1 to 7, wherein the concentration of the alkanesulfonic acid used as solvent is at least 80 weight percent.
9. Process according to item 8, wherein the concentration of the alkanesulfonic acid used as solvent is at least about 90 weight percent.
10. Process according to any one of items 1 to 9, wherein, for the oxidation, air, a gas stream enriched with oxygen in free form, and/or pure oxygen in free form is fed in.
11. Process according to item 10, wherein, for the oxidation, a gas stream comprising oxygen, containing more than 21 vol.-% of oxygen in free form, is fed in.
12. Process according to any one of items 1 to 11, wherein the process is carried out at a pressure of more than 1 bara to about 20 bara.
13. Process according to item 12, wherein the process is carried out at a pressure of more than 2 bara to about 15 bara.
14. Process according to any one of items 1 to 13, wherein a solubilizer between the dialkyl disulfide and the alkanesulfonic acid is used.
15. Process according to item 14, wherein alkanesulfonic acid S-alkyl ester of the formula $R-SO_2-S-R$ is used as solubilizer between the dialkyl disulfide and the alkanesulfonic acid, with the alkyl radicals of the alkanesulfonic acid S-alkyl ester being identical with the alkyl radicals of the dialkyl disulfide to be converted and with the alkyl radical of the alkanesulfonic acid.

FIGURES

FIG. 1 shows the sample temperature in ° C. as a function of the time in seconds in a pressure/heat accumulation test (experiment 23) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 2:
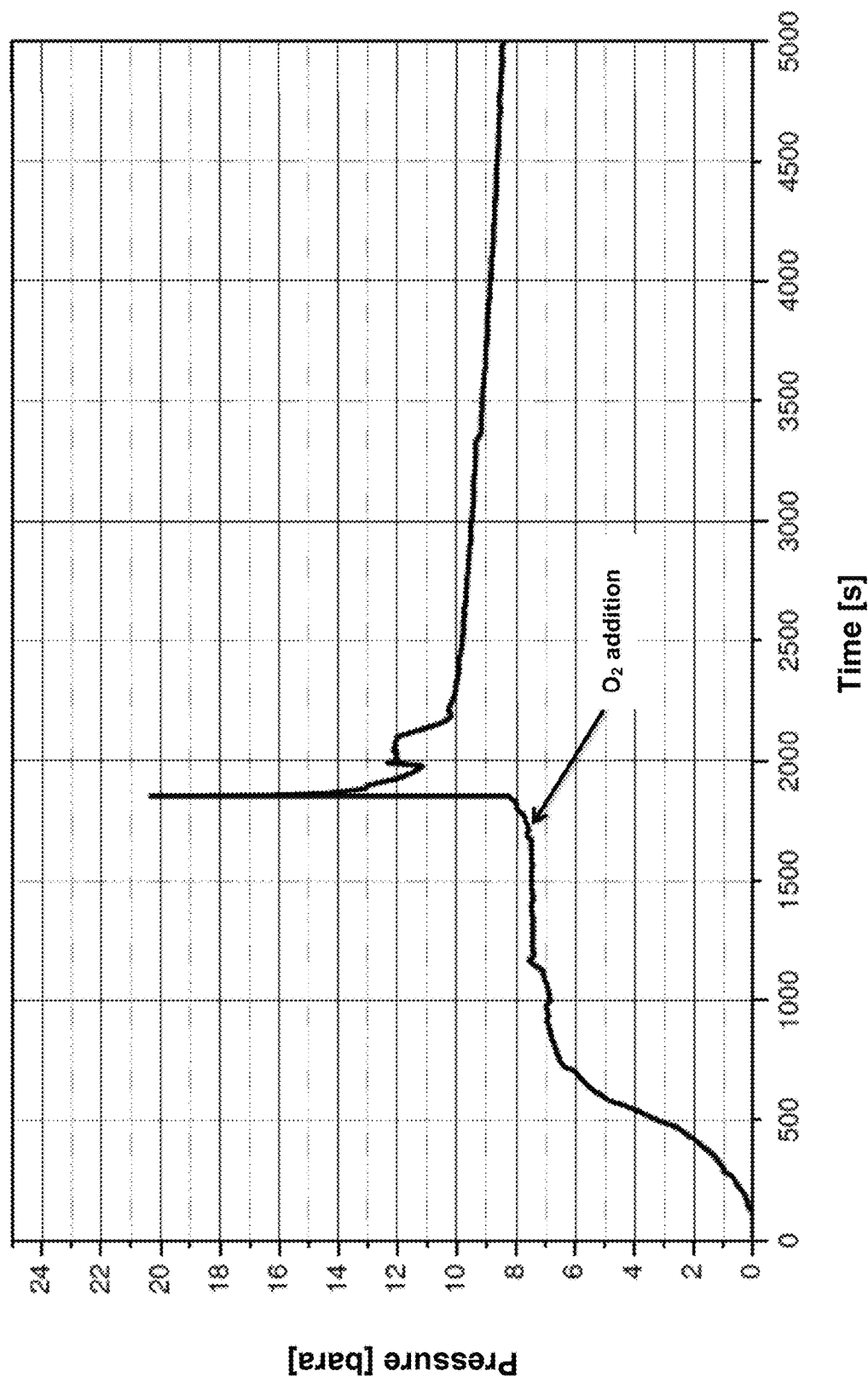

FIG. 2 shows the pressure in bara as a function of the time in seconds in a pressure/heat accumulation test (experiment 23) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 3:
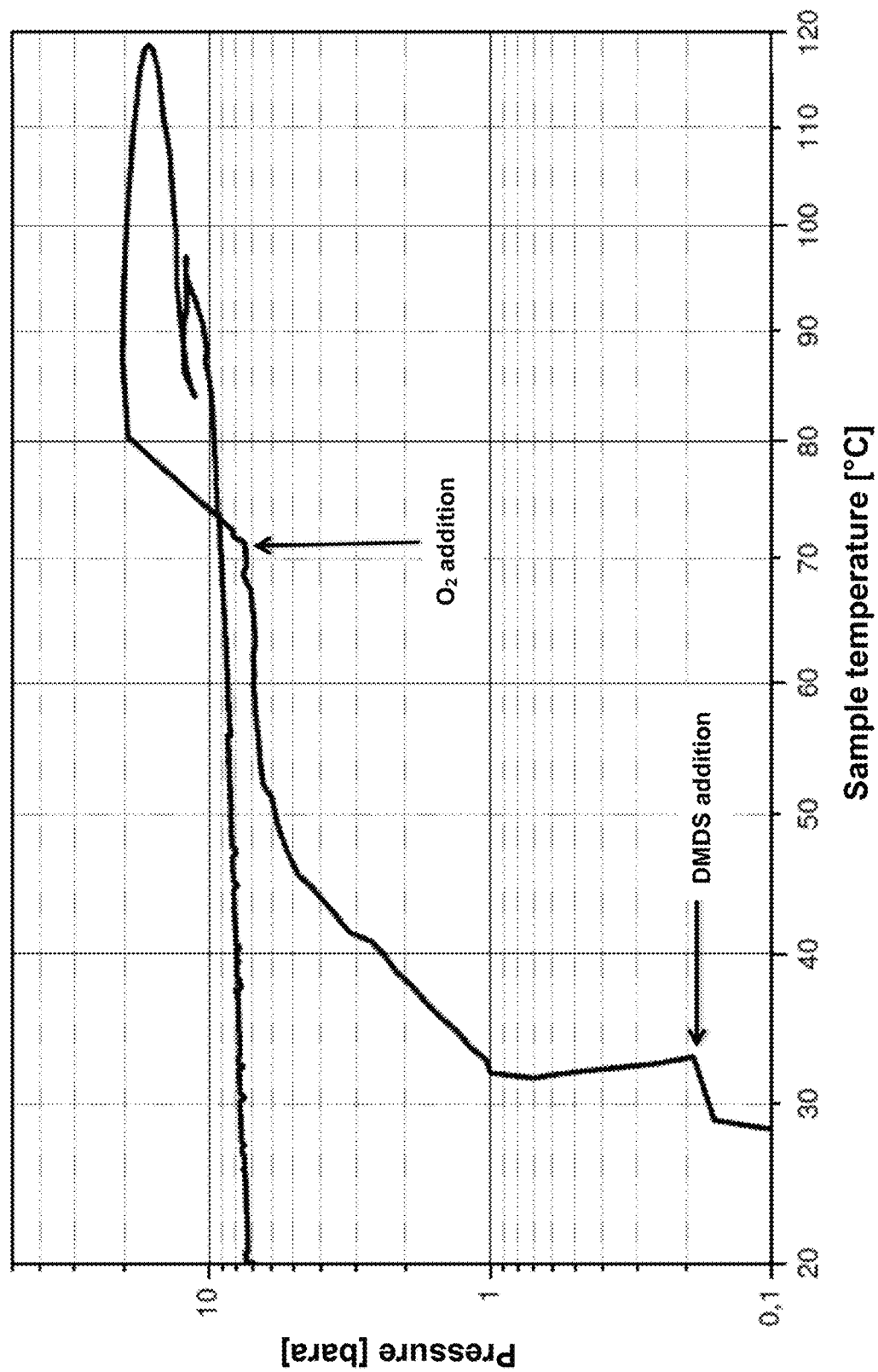

FIG. 3 shows the pressure in bara as a function of the sample temperature in ° C. in a pressure/heat accumulation test (experiment 23) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 4:
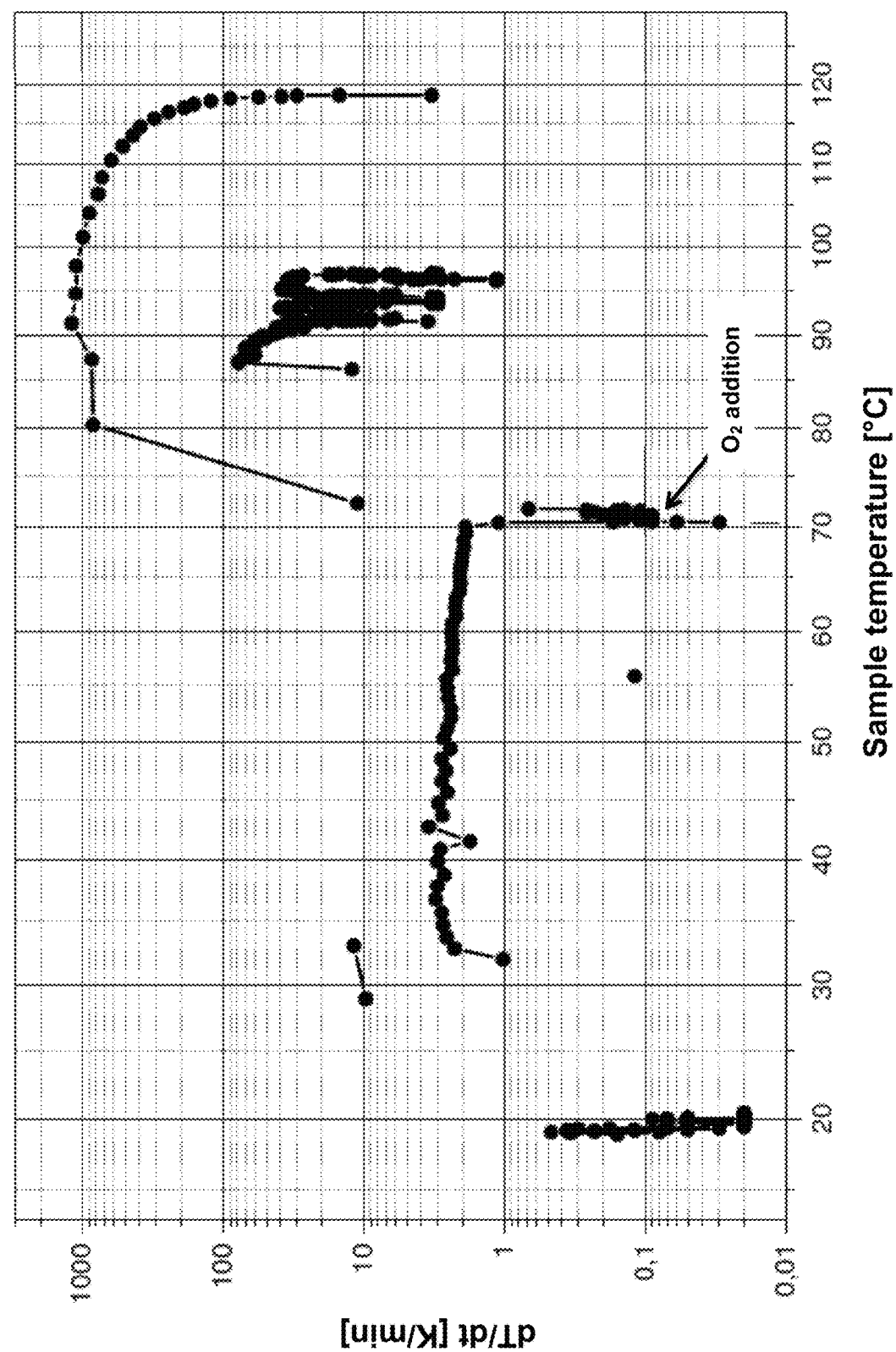

FIG. 4 shows the time-dependent change in temperature in K/min as a function of the sample temperature in ° C. in a pressure/heat accumulation test (experiment 23) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 5:
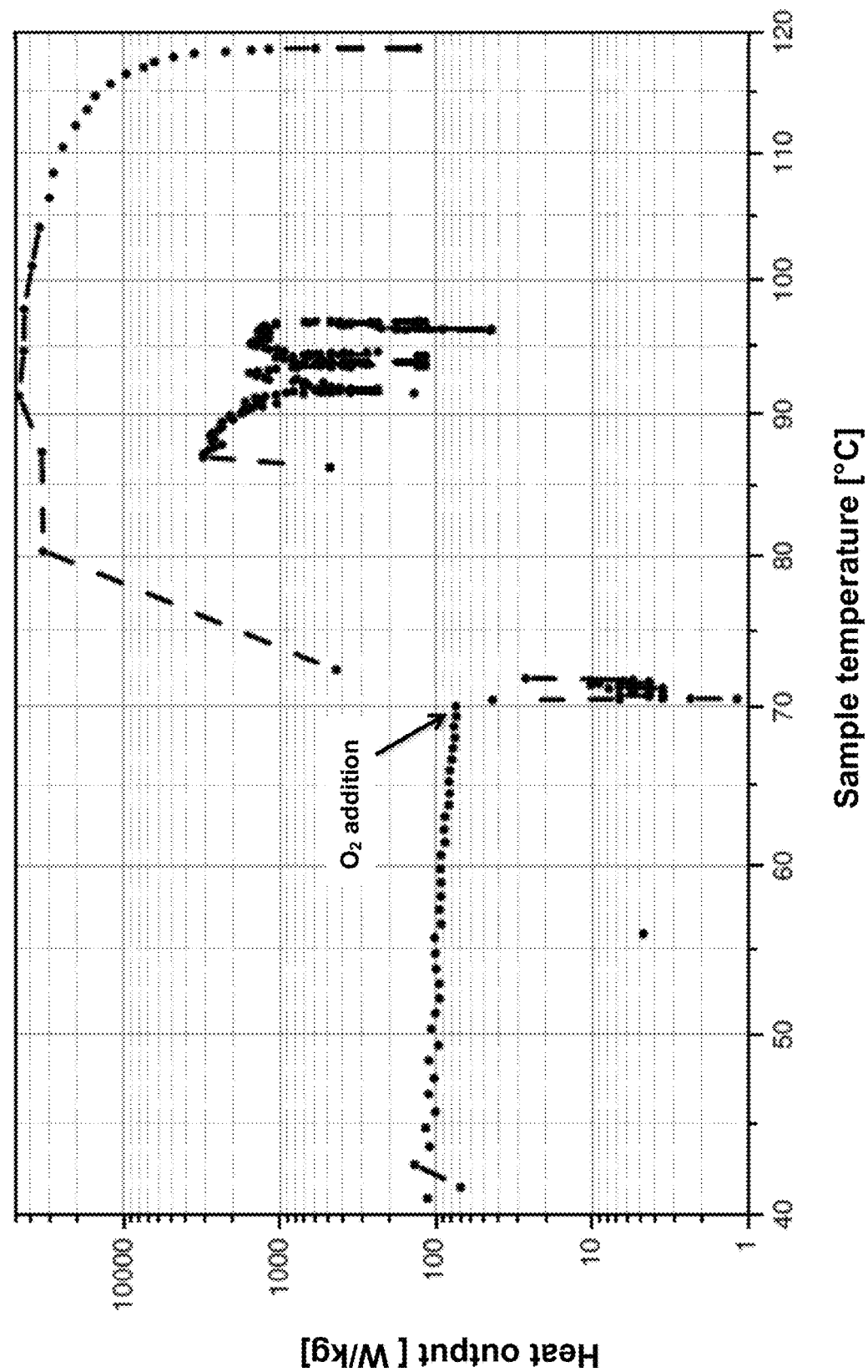

FIG. 5 shows the heat output in W/kg as a function of the sample temperature in ° C. in a pressure/heat accumulation test (experiment 23) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 6:
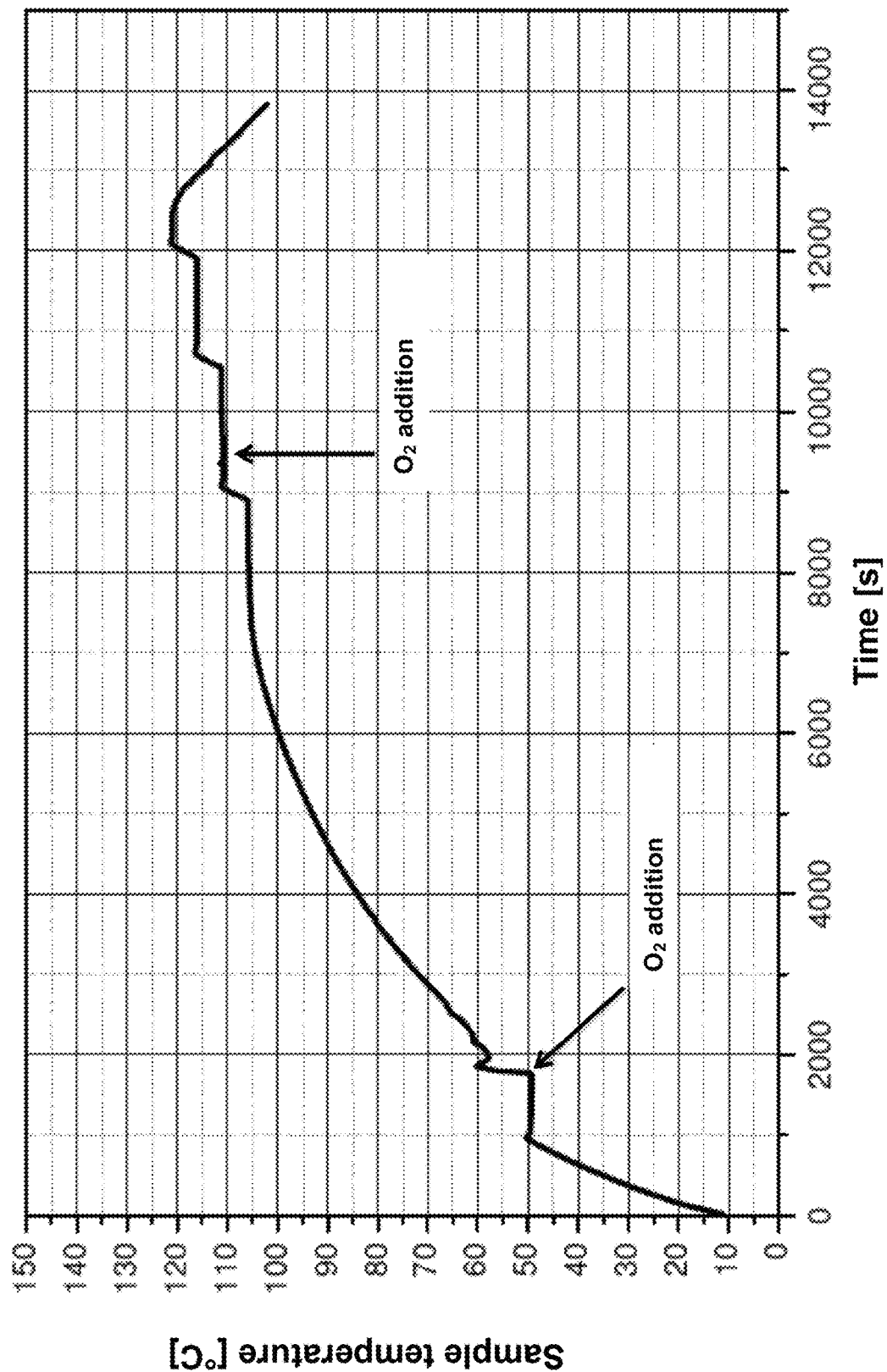

FIG. 6 shows the sample temperature in ° C. as a function of the time in seconds in a pressure/heat accumulation test (experiment 24) in an adiabatic calorimeter (Phi-TEC II). The material investigated was the reaction effluent from experiment 23, with the following
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 7:
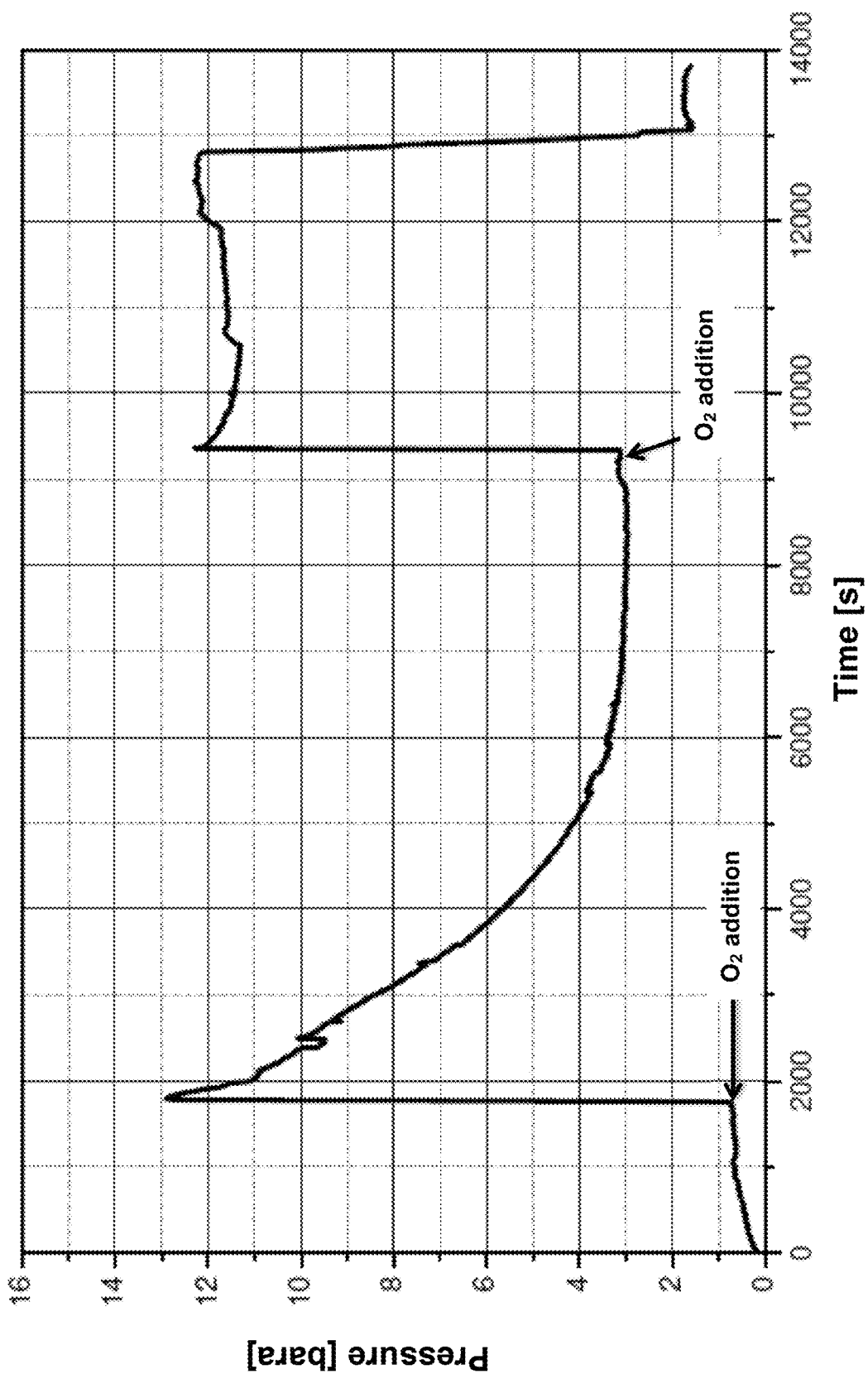

FIG. 7 shows the pressure in bara as a function of the time in seconds in a pressure/heat accumulation test (experiment 24) in an adiabatic calorimeter (Phi-TEC II). The material investigated was the reaction effluent from experiment 23, with the following
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 8:
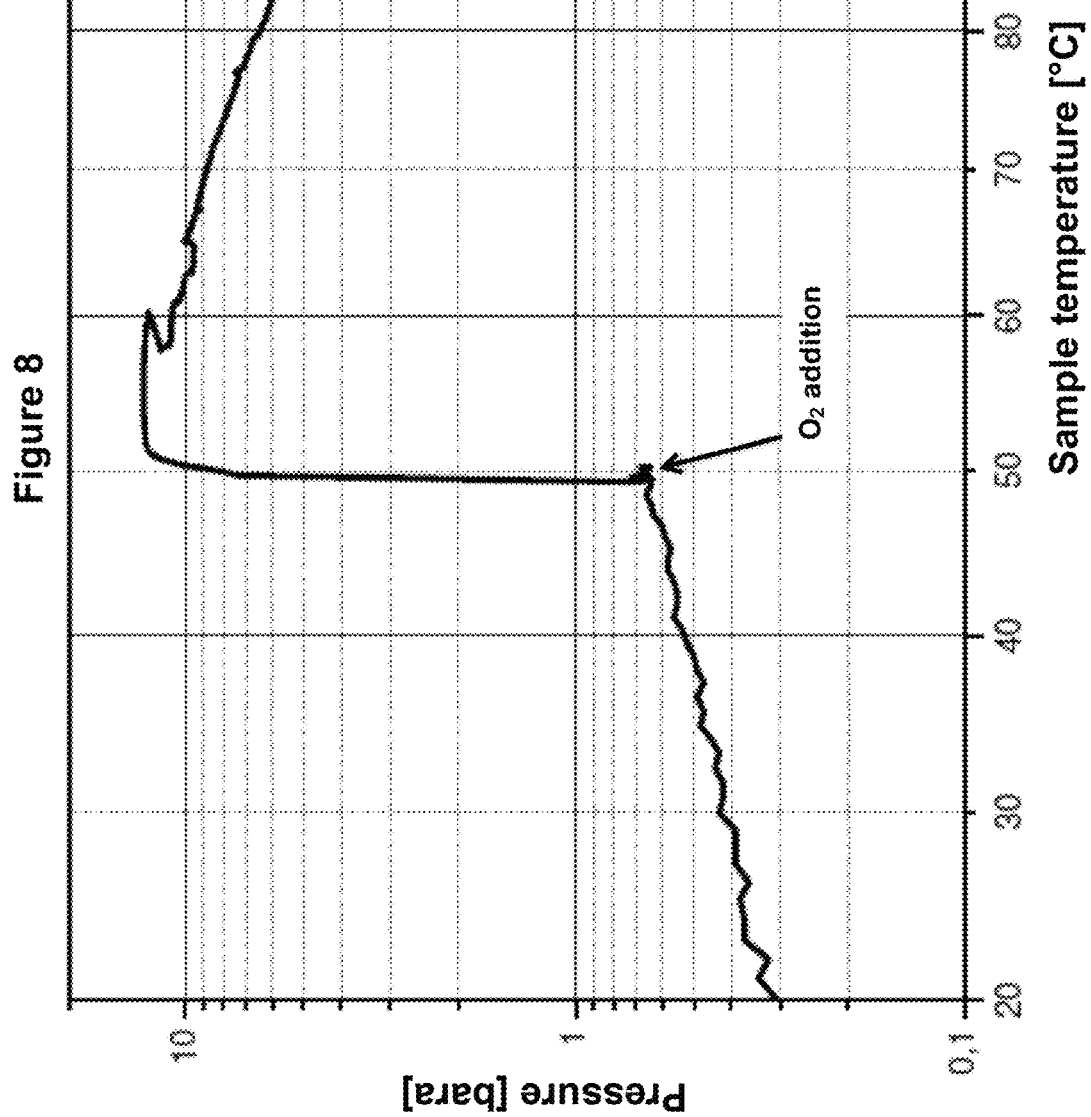

FIG. 8 shows the pressure in bara as a function of the sample temperature in ° C. in a pressure/heat accumulation test (experiment 24) in an adiabatic calorimeter (Phi-TEC II). The material investigated was the reaction effluent from experiment 23, with the following
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 9:
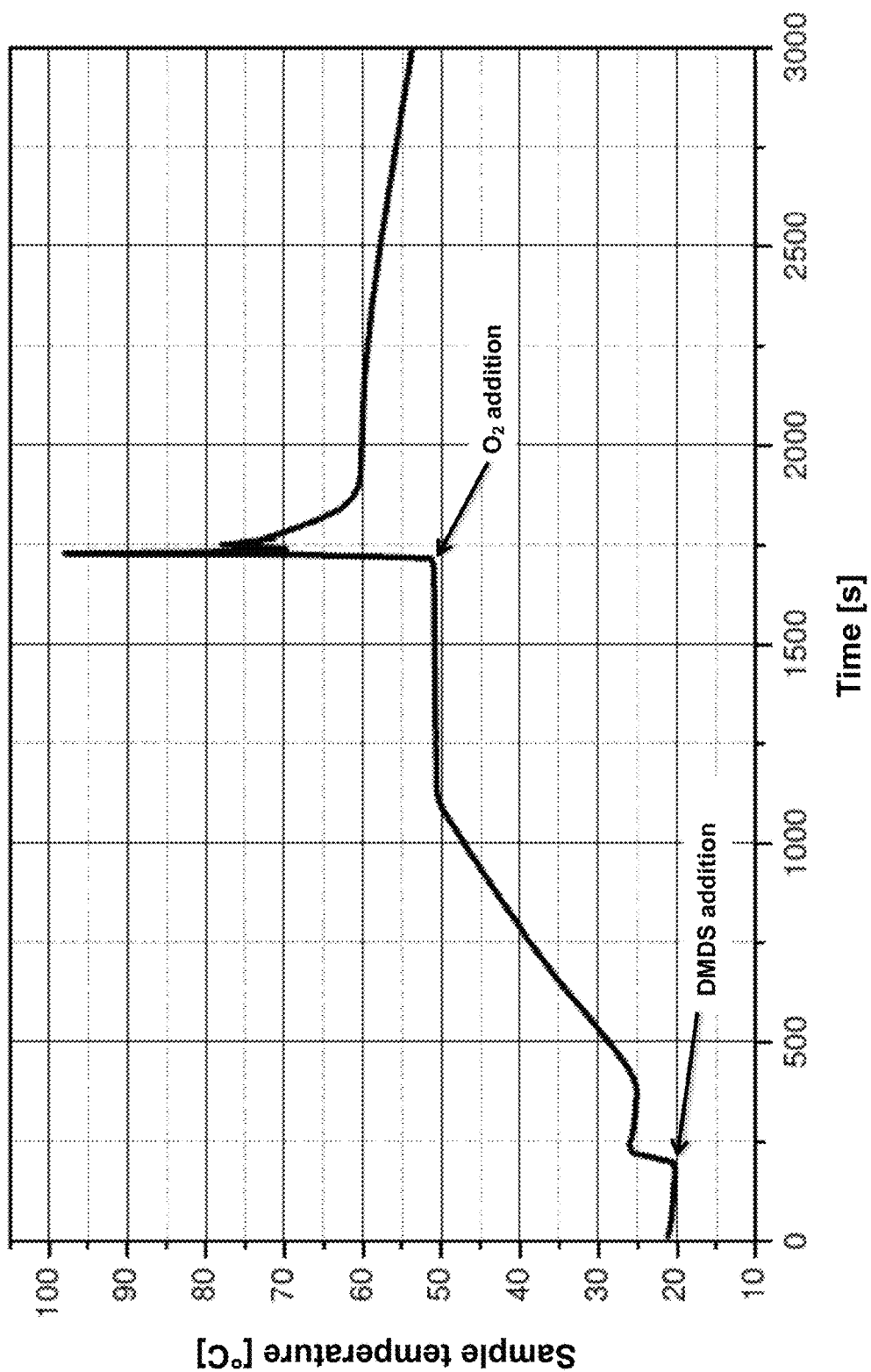

FIG. 9 shows the sample temperature in ° C. as a function of the time in seconds in a pressure/heat accumulation test (experiment 25) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 10:
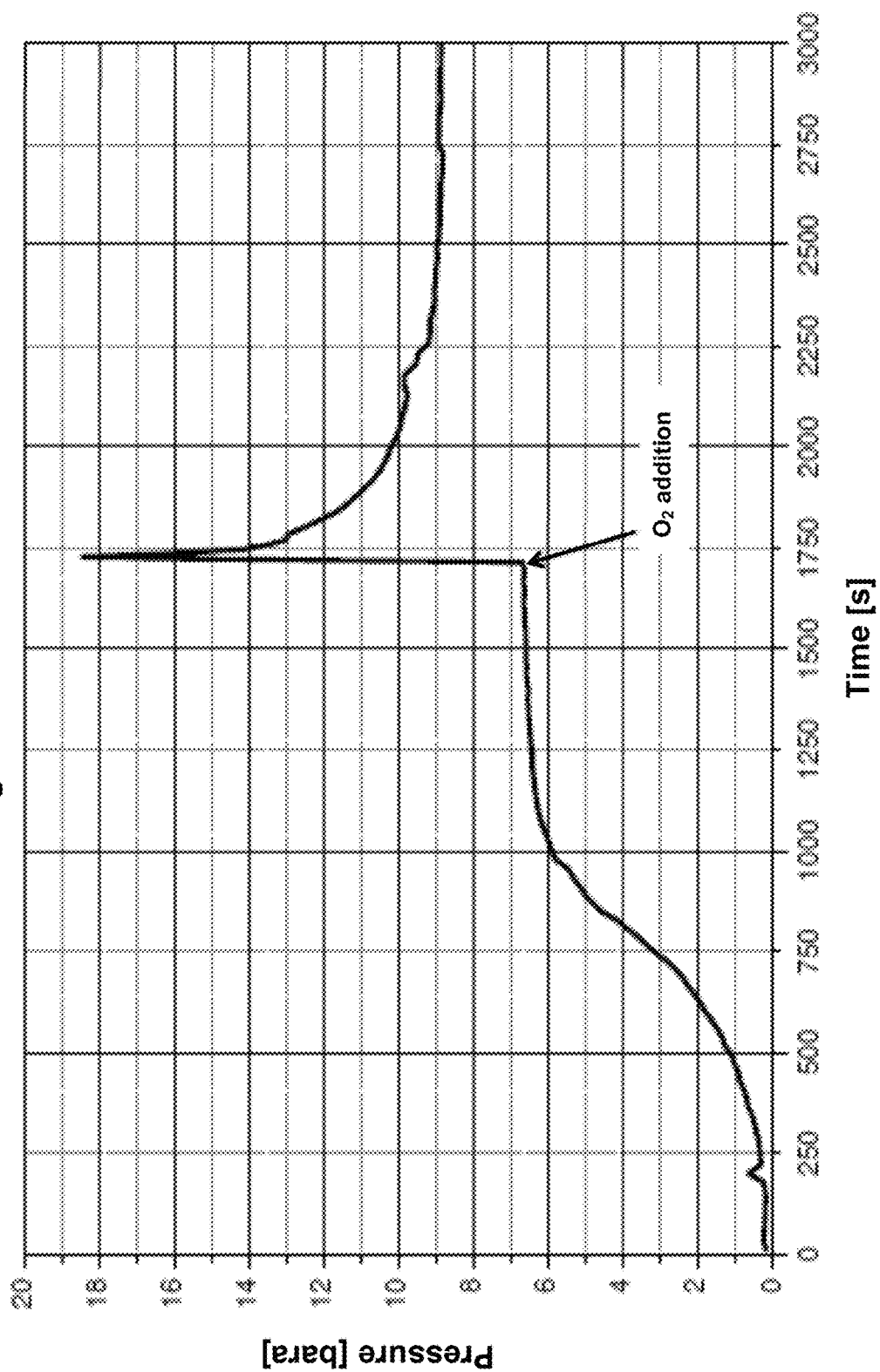

FIG. 10 shows the pressure in bara as a function of the time in seconds in a pressure/heat accumulation test (experiment 25) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 11:
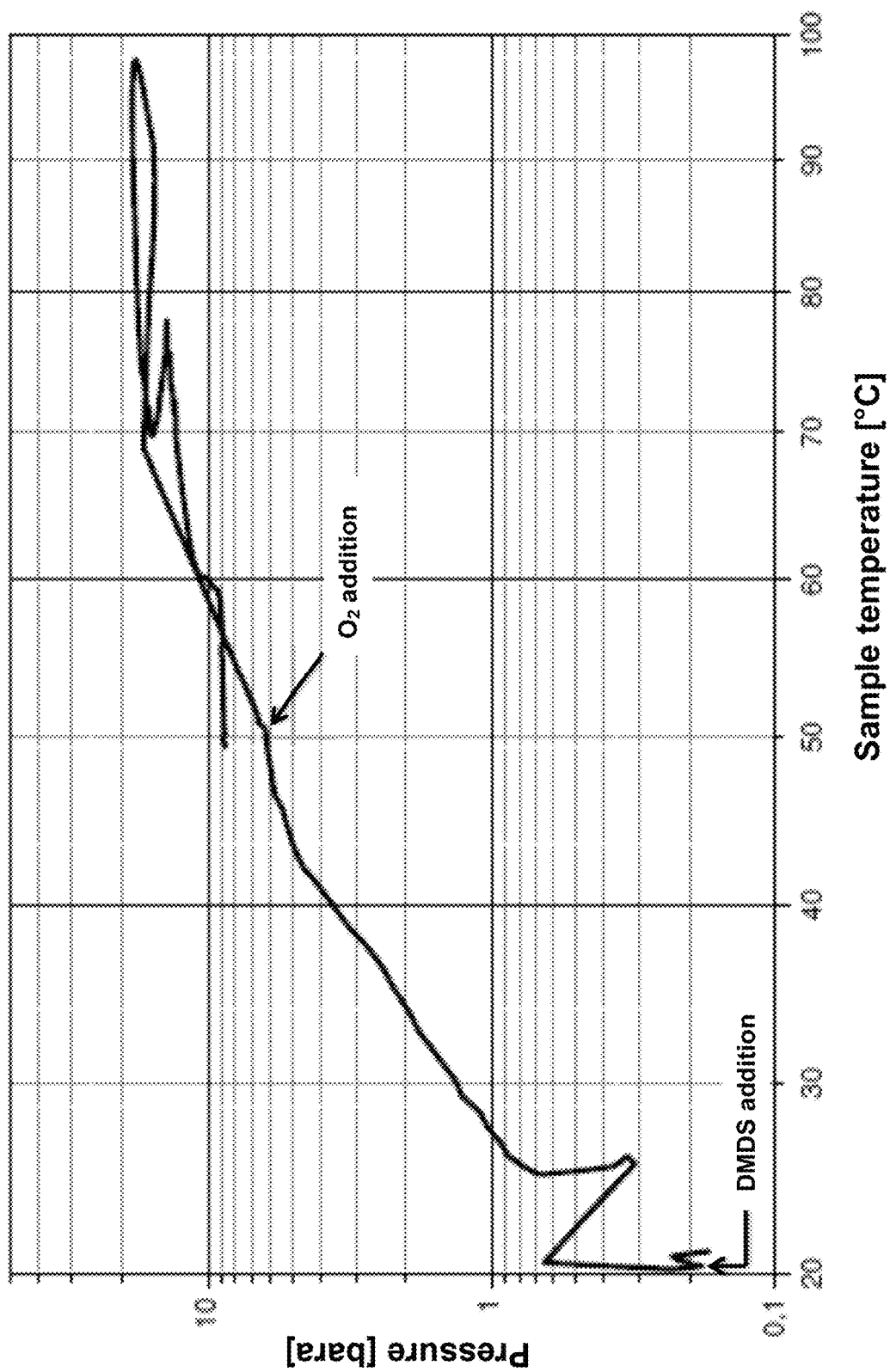

FIG. 11 shows the pressure in bara as a function of the sample temperature in ° C. in a pressure/heat accumulation test (experiment 25) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 12:
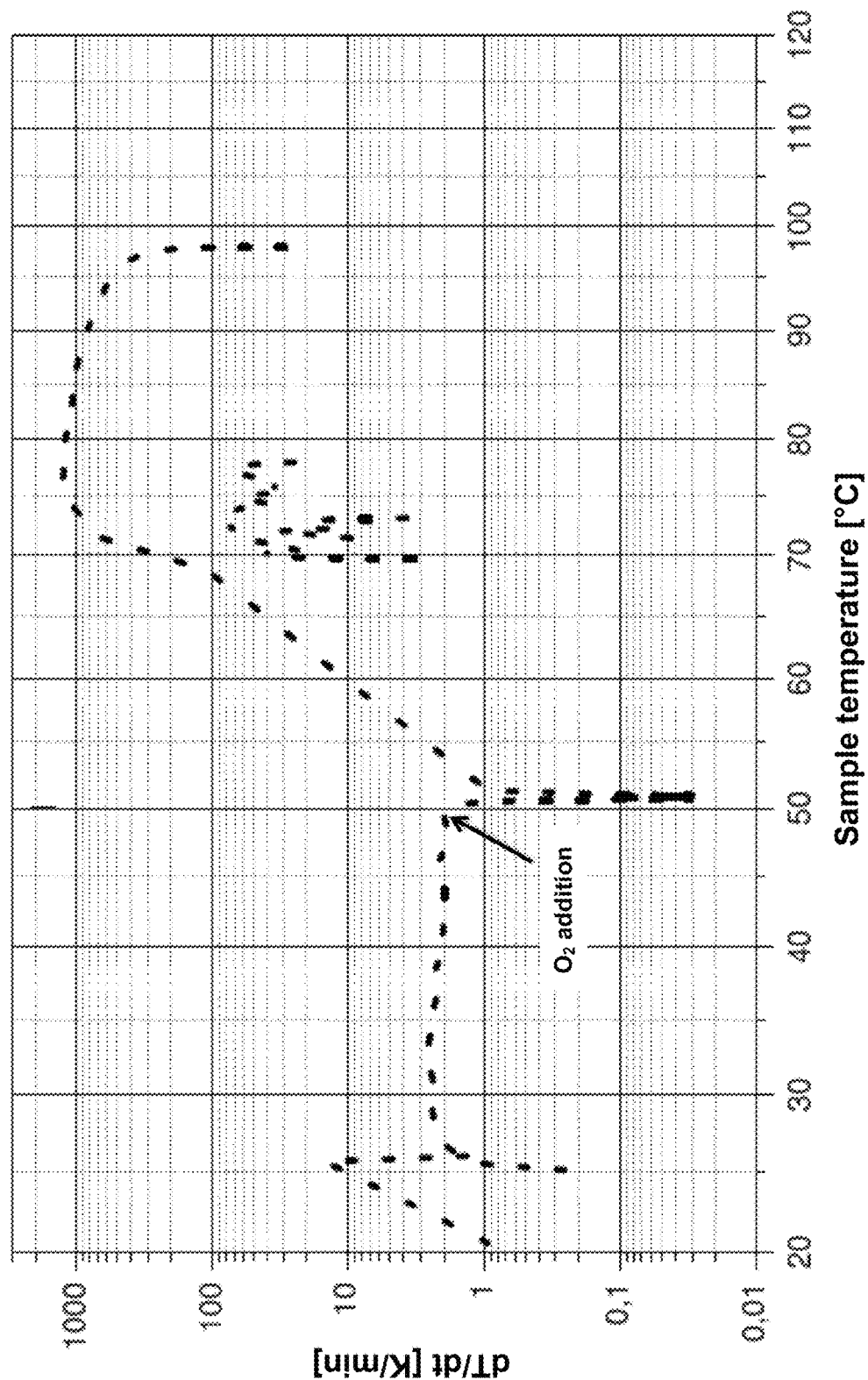

FIG. 12 shows the time-dependent change in temperature in K/min as a function of the sample temperature in ° C. in a pressure/heat accumulation test (experiment 25) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 13:
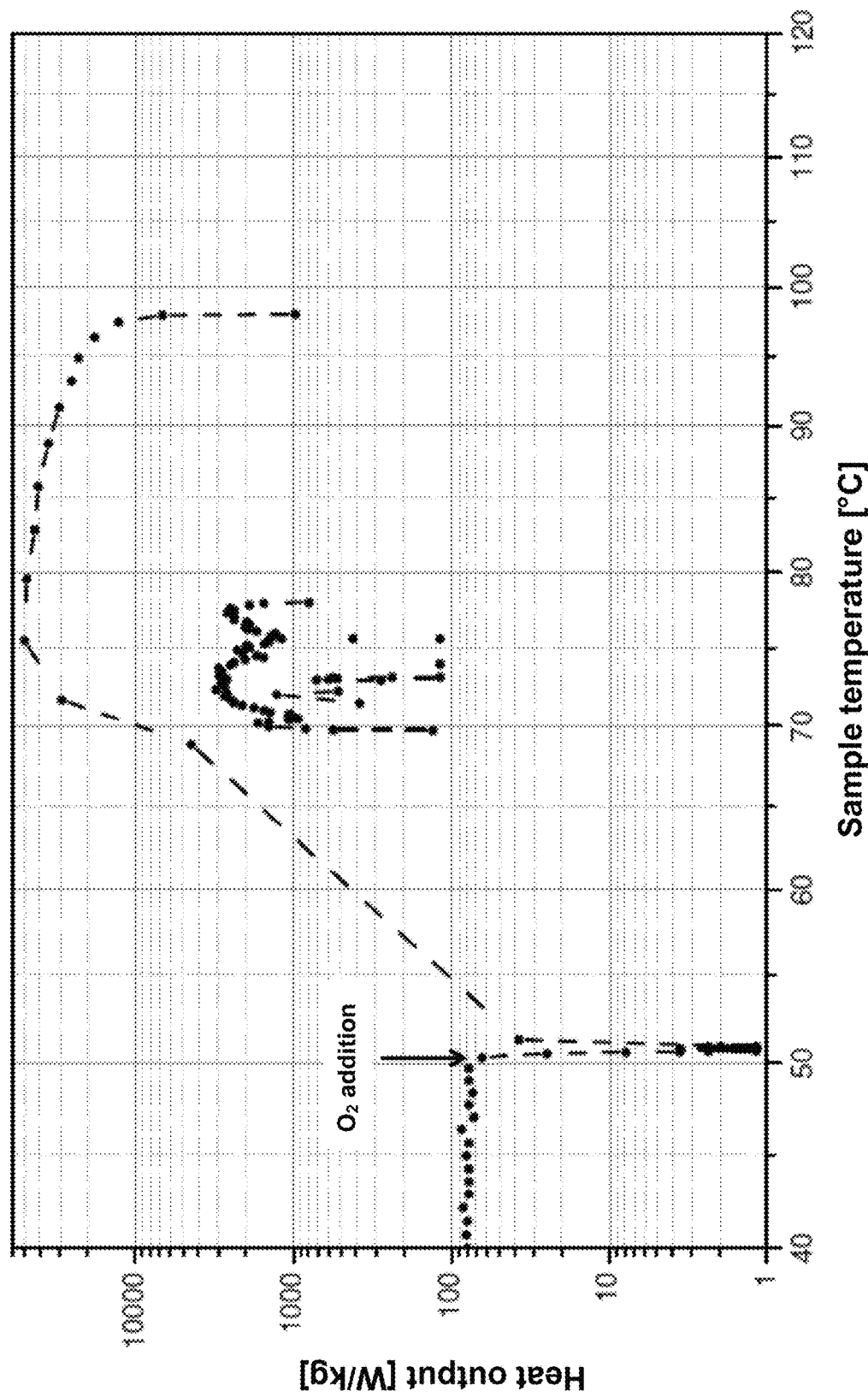

FIG. 13 shows the heat output in W/kg as a function of the sample temperature in ° C. in a pressure/heat accumulation test (experiment 25) in an adiabatic calorimeter (Phi-TEC II).
Sample composition: 79.2 g methanesulfonic acid/21.38 g dimethyl disulfide/5 g $H_2O$/1.1 g $HNO_3$ (65%)/$O_2$
Closed sample container: Hastelloy C 276 with a volume of 115 ml
Total sample volume: about 80 ml
Sample container fill level: about 70%

Figure 14:
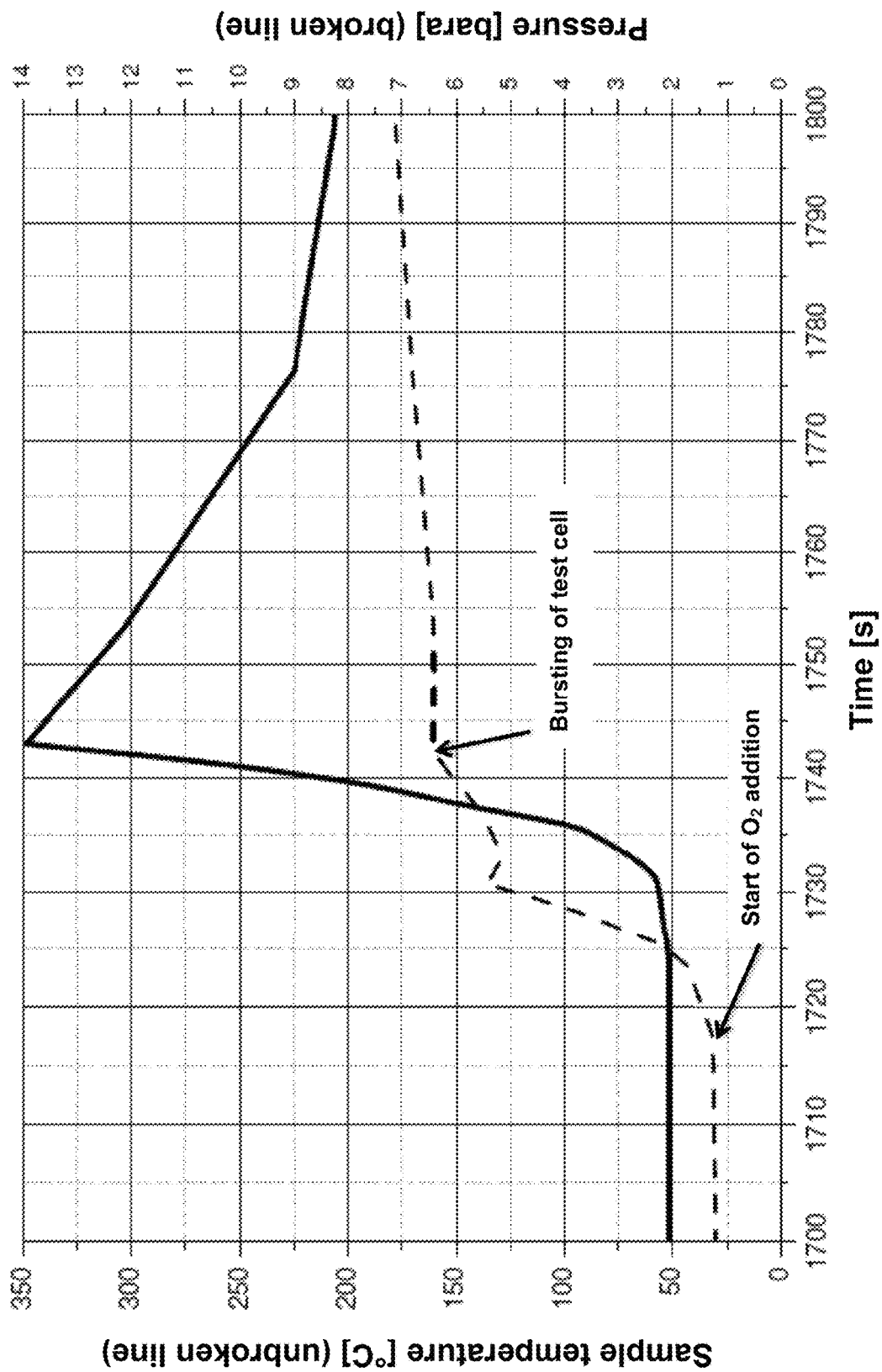

FIG. 14 shows the sample temperature in ° C. (continuous line) and the pressure in bara (interrupted line) as a function of the time in seconds in a pressure/heat accumulation test (experiment 26) in an adiabatic calorimeter (Phi-TEC II).

Sample composition: 79.2 g methanesulfonic acid/21.38 g dimethyl disulfide/5 g $H_2O$/1.1 g $HNO_3$ (65%)/$O_2$ Closed sample container: Stainless steel 1.4571 with a volume of 110 ml Total sample volume: about 80 ml Sample container fill level: about 73%

Figure 15:
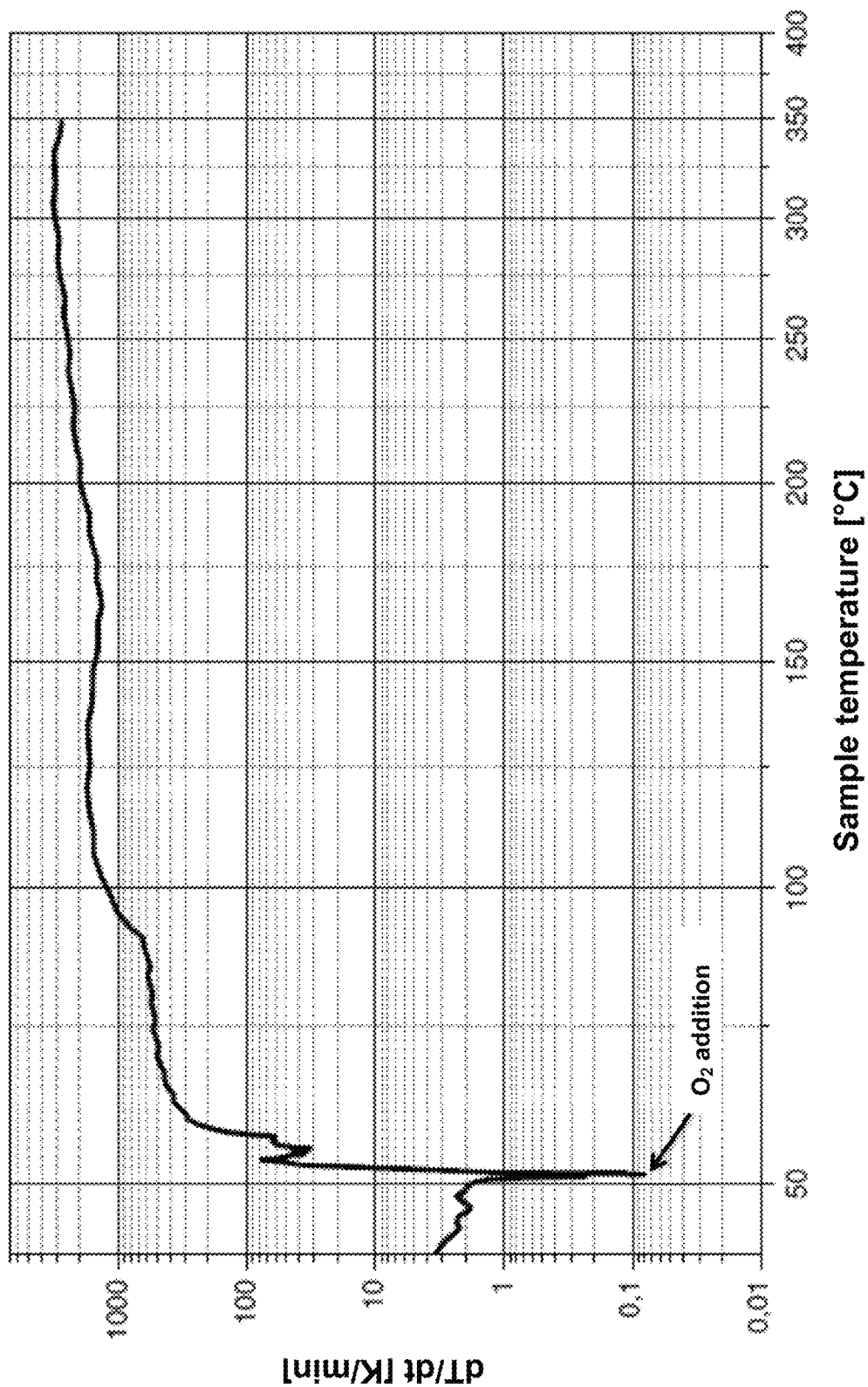

FIG. 15 shows the time-dependent change in temperature in K/min as a function of the sample temperature in ° C. in a pressure/heat accumulation test (experiment 26) in an adiabatic calorimeter (Phi-TEC II).

Sample composition: 79.2 g methanesulfonic acid/21.38 g dimethyl disulfide/5 g $H_2O$/1.1 g $HNO_3$ (65%)/$O_2$ Closed sample container: Stainless steel 1.4571 with a volume of 110 ml Total sample volume: about 80 ml Sample container fill level: about 73%

Figure 16:
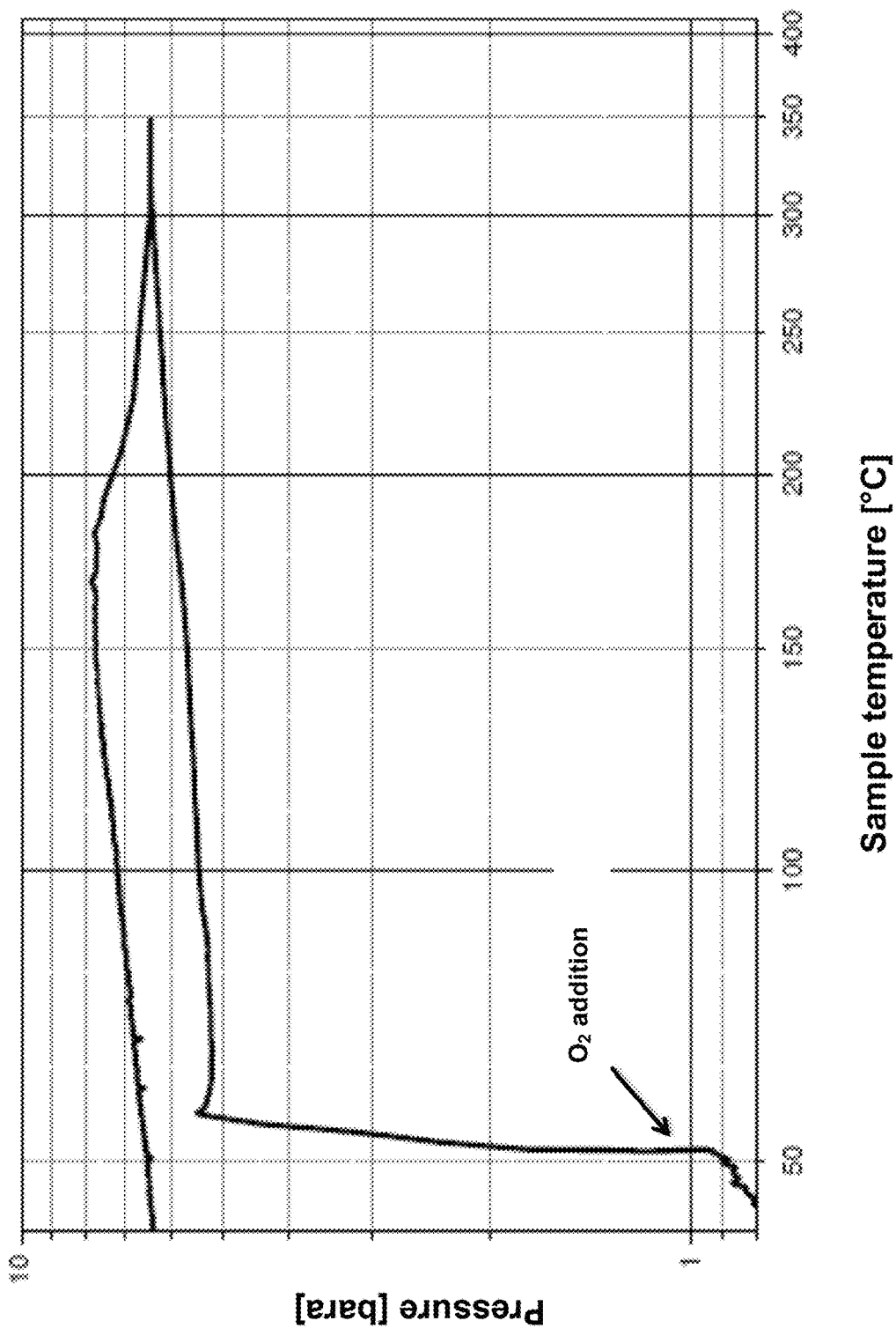

FIG. 16 shows the pressure in bara as a function of the sample temperature in ° C. in a pressure/heat accumulation test (experiment 26) in an adiabatic calorimeter (Phi-TEC II).

Sample composition: 79.2 g methanesulfonic acid/21.38 g dimethyl disulfide/5 g $H_2O$/1.1 g $HNO_3$ (65%)/$O_2$ Closed sample container: Stainless steel 1.4571 with a volume of 110 ml Total sample volume: about 80 ml Sample container fill level: about 73%

Figure 17:
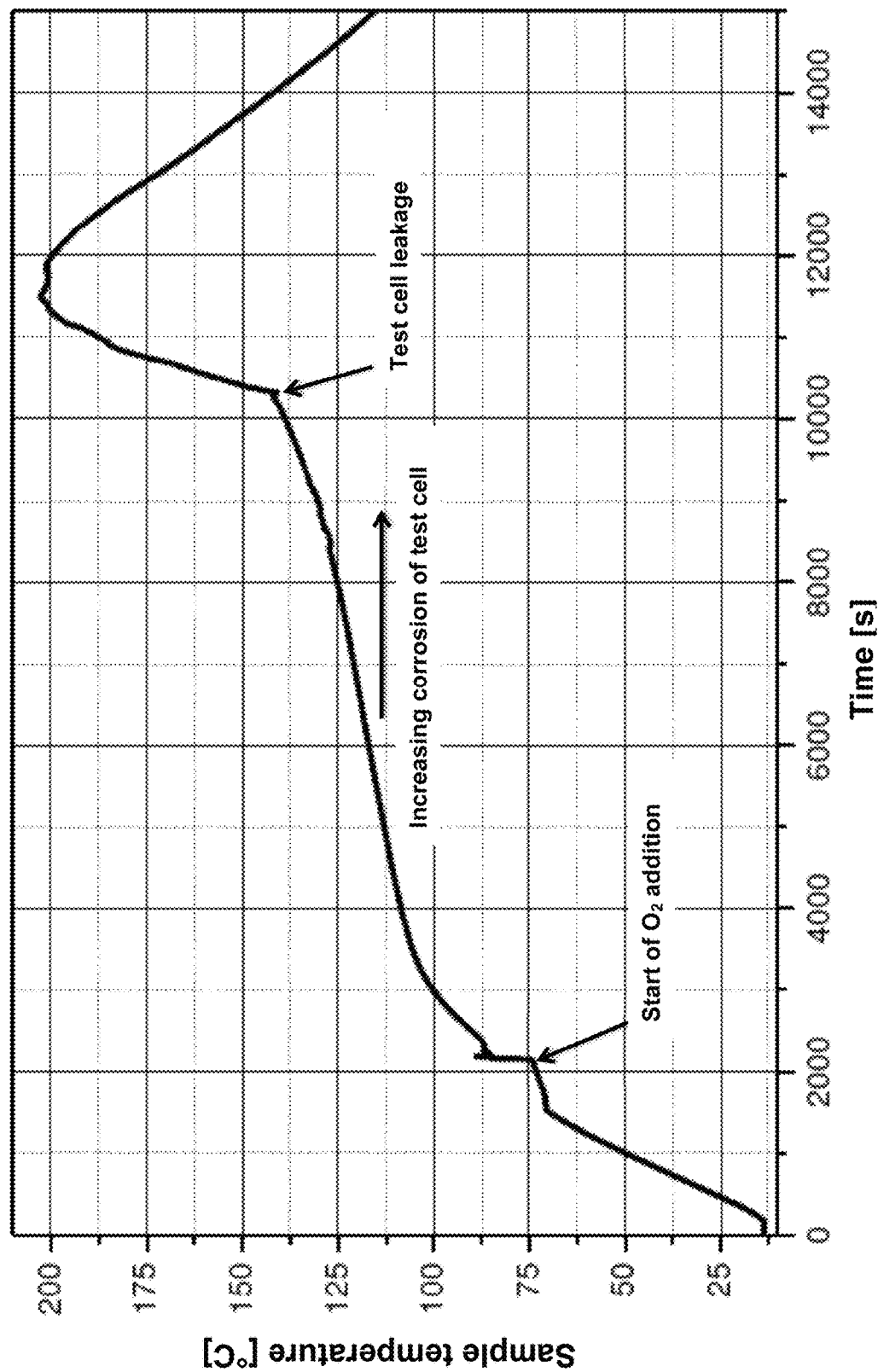

FIG. 17 shows the sample temperature in ° C. as a function of the time in seconds in a pressure/heat accumulation test (experiment 27) in an adiabatic calorimeter (Phi-TEC II).

Sample composition: 110.67 g methanesulfonic acid/11.0 g dimethyl disulfide/2.6 g $H_2O$/0.57 g $HNO_3$ (65%)/$O_2$ Closed sample container: Hastelloy C276 with a volume of 115 ml Total sample volume: about 81 ml Sample container fill level: about 74%

Figure 18:
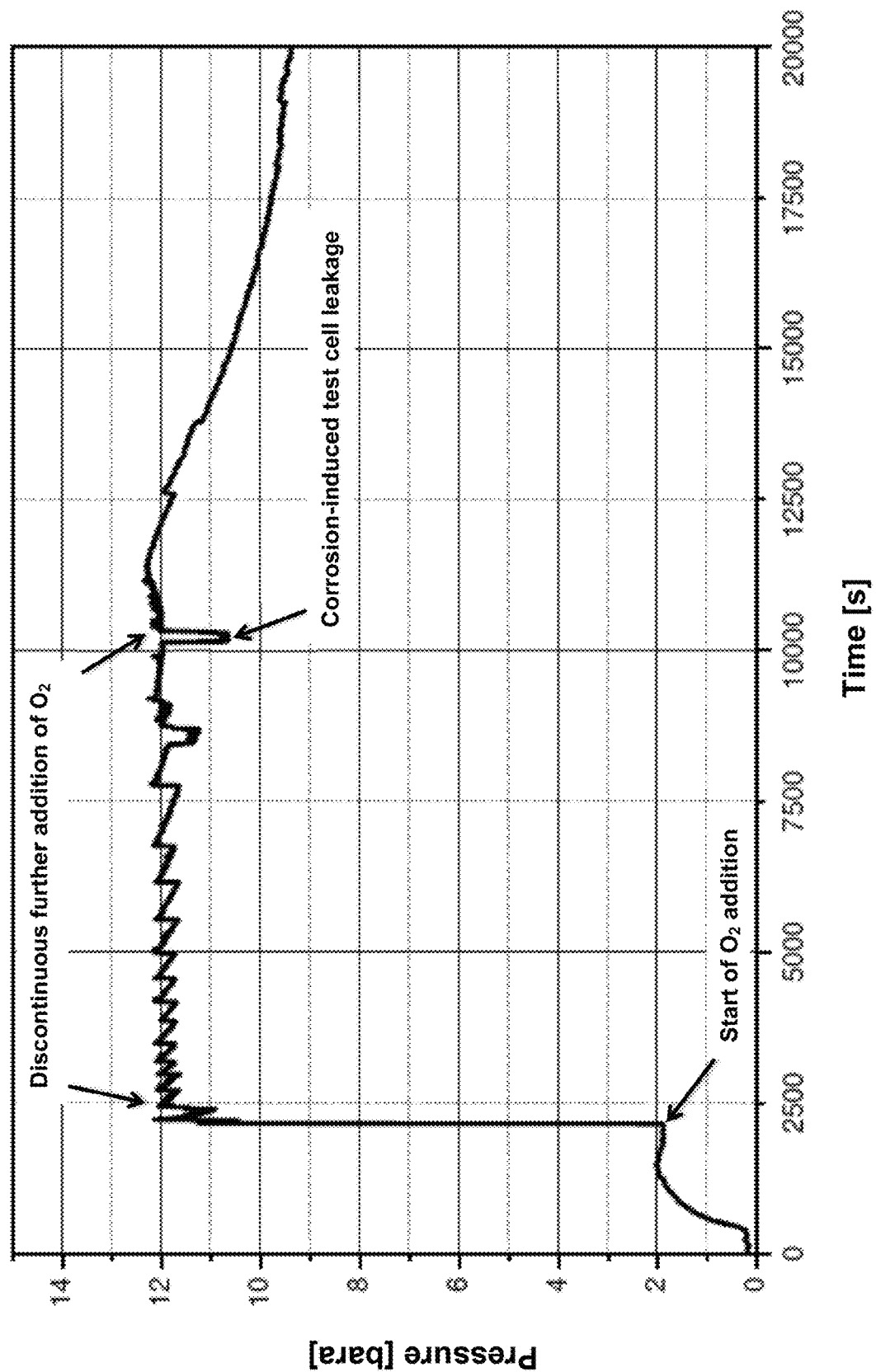

FIG. 18 shows the pressure in bara as a function of the time in seconds in a pressure/heat accumulation test (experiment 27) in an adiabatic calorimeter (Phi-TEC II).

Sample composition: 110.67 g methanesulfonic acid/11.0 g dimethyl disulfide/2.6 g $H_2O$/0.57 g $HNO_3$ (65%)/$O_2$ Closed sample container: Hastelloy C276 with a volume of 115 ml Total sample volume: about 81 ml Sample container fill level: about 74%

Figure 19:
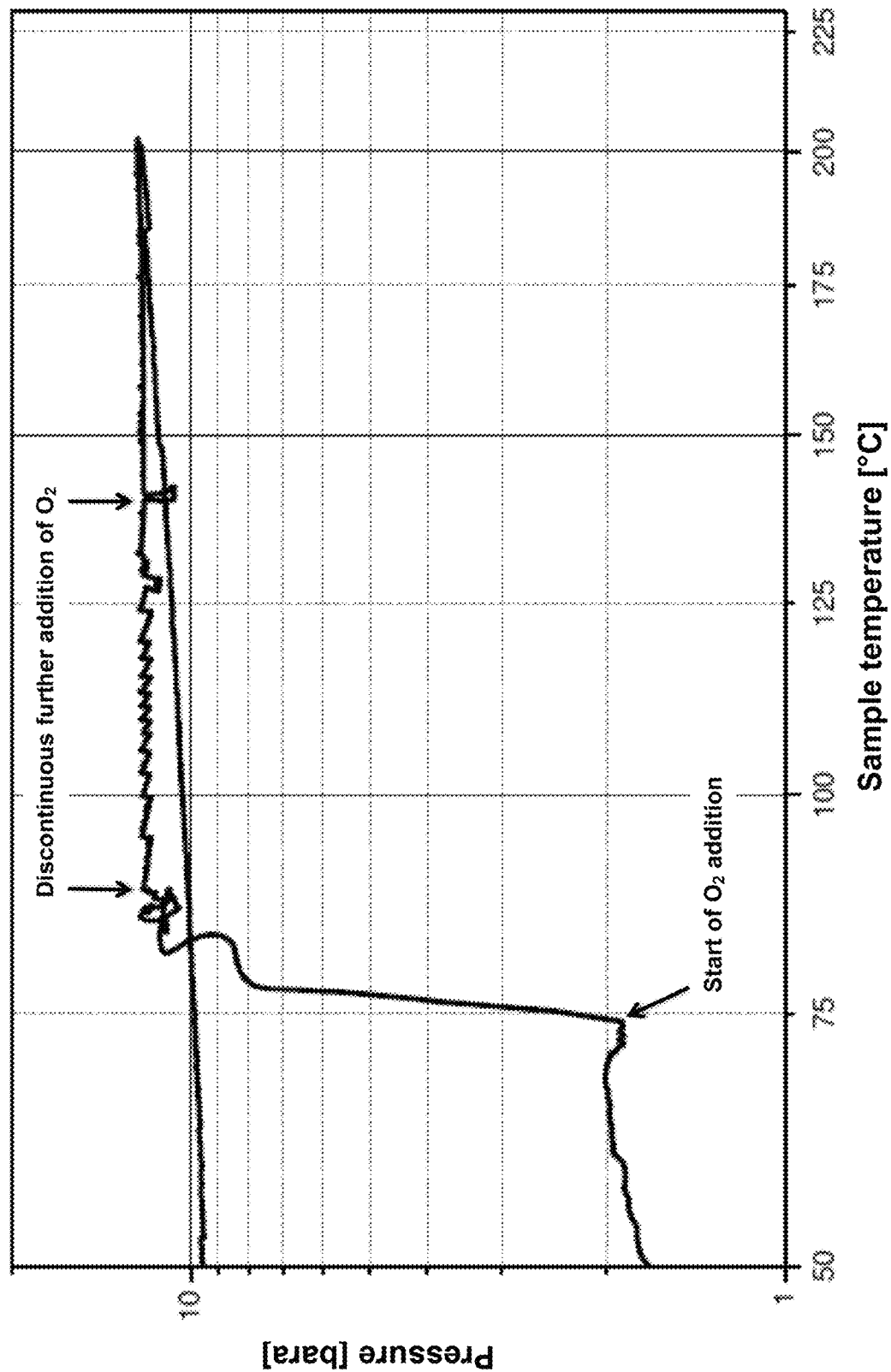

FIG. 19 shows the pressure in bara as a function of the sample temperature in ° C. in a pressure/heat accumulation test (experiment 27) in an adiabatic calorimeter (Phi-TEC II).

Sample composition: 110.67 g methanesulfonic acid/11.0 g dimethyl disulfide/2.6 g $H_2O$/0.57 g $HNO_3$ (65%)/$O_2$ Closed sample container: Hastelloy C276 with a volume of 115 ml Total sample volume: about 81 ml Sample container fill level: about 74%

Figure 20:
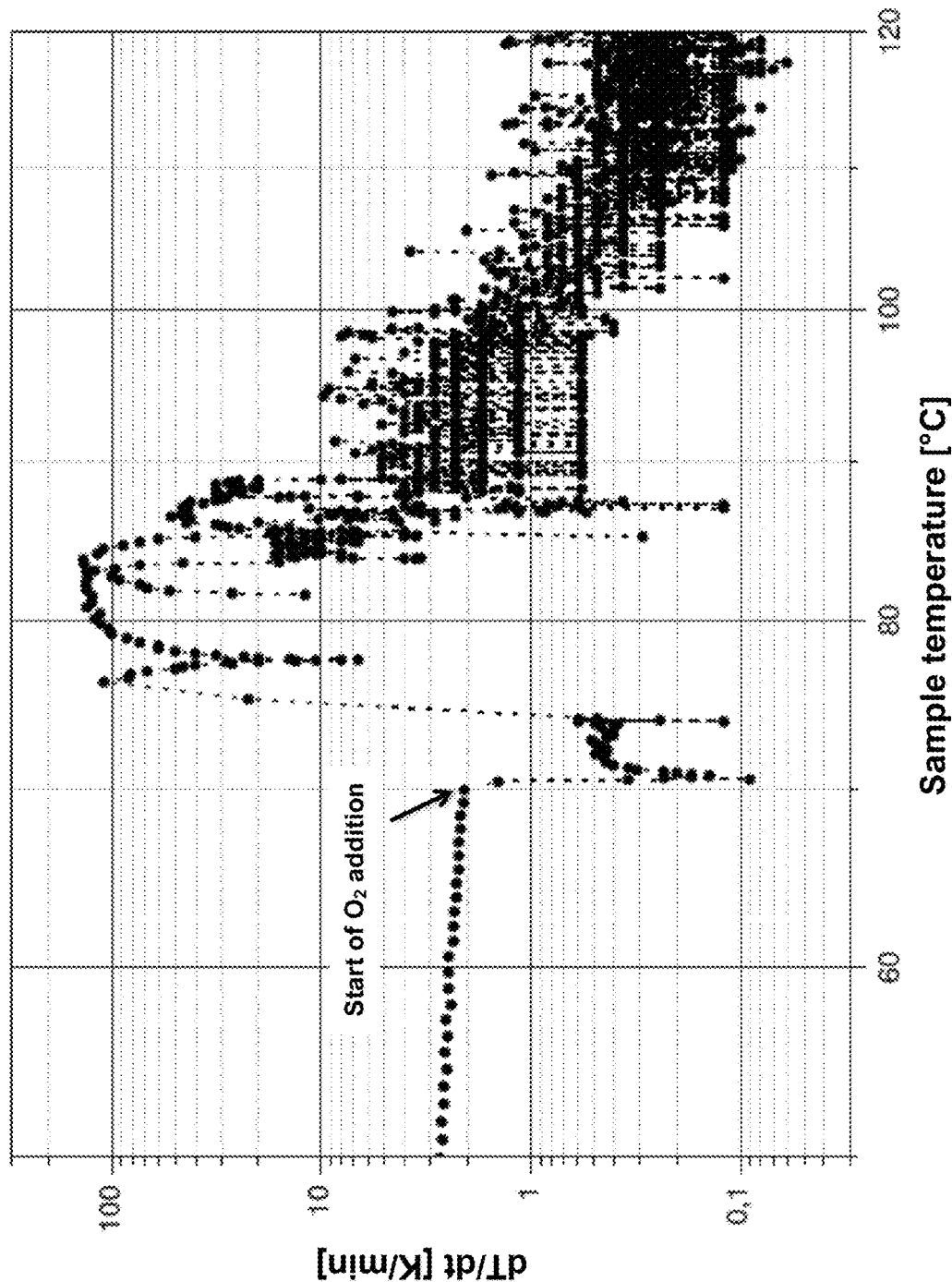

FIG. 20 shows the time-dependent change in temperature in K/min as a function of the sample temperature in ° C. in a pressure/heat accumulation test (experiment 27) in an adiabatic calorimeter (Phi-TEC II).

Sample composition: 110.67 g methanesulfonic acid/11.0 g dimethyl disulfide/2.6 g $H_2O$/0.57 g $HNO_3$ (65%)/$O_2$ Closed sample container: Hastelloy C276 with a volume of 115 ml Total sample volume: about 81 ml Sample container fill level: about 74%

TABLE 1

Summary of the various diagrams of FIGS. 1 to 20.

| FIG. | Experiment No. | Representation |
| --- | --- | --- |
| 1 | 23 | Sample temperature in ° C. as function of time in seconds |
| 2 | 23 | Pressure in bara as function of time in seconds |
| 3 | 23 | Pressure in bara as function of the sample temperature in ° C. |
| 4 | 23 | Time-dependent change in temperature in K/min as function of the sample temperature in ° C. |
| 5 | 23 | Heat output in W/kg as function of the sample temperature in ° C. |
| 6 | 24 | Sample temperature in ° C. as function of time in seconds |
| 7 | 24 | Pressure in bara as function of time in seconds |
| 8 | 24 | Pressure in bara as function of the sample temperature in ° C. |
| 9 | 25 | Sample temperature in ° C. as function of time in seconds |
| 10 | 25 | Pressure in bara as function of time in seconds |
| 11 | 25 | Pressure in bara as function of the sample temperature in ° C. |
| 12 | 25 | Time-dependent change in temperature in K/min as function of the sample temperature in ° C. |
| 13 | 25 | Heat output in W/kg as function of the sample temperature in ° C. |
| 14 | 26 | Sample temperature in ° C. (unbroken line) and pressure in bara (broken line) as function of time in seconds |
| 15 | 26 | Time-dependent change in temperature in K/min as function of the sample temperature in ° C. |
| 16 | 26 | Pressure in bara as function of the sample temperature in ° C. |
| 17 | 27 | Sample temperature in ° C. as function of time in seconds |
| 18 | 27 | Pressure in bara as function of time in seconds |
| 19 | 27 | Pressure in bara as function of the sample temperature in ° C. |
| 20 | 27 | Time-dependent change in temperature in K/min as function of the sample temperature in ° C. |

EXAMPLES

A) Suitability of Methanesulfonic Acid as Solvent in the Oxidation of Dimethyl Disulfide Methanesulfonic acid was investigated in 10 experiments for its suitability as a solvent in the preparation of methanesulfonic acid by oxidation of dimethyl disulfide. This was done by preparing solutions of different amounts of dimethyl disulfide in methanesulfonic acid, nitric acid (65 wt.-%) and small amounts of water and transferring them to an autoclave. The conversion of the dimethyl disulfide to the methanesulfonic acid took place at temperatures of 50° C. to 90° C. and at pressures of 3 bara up to 12 bara oxygen. For this purpose, oxygen was introduced into each of the samples via an immersion tube, and a stirrer was used to ensure optimum distribution in the reaction mixture. The individual compositions of the reaction mixtures in experiments 1 to 10, and the specific reaction conditions in these reactions, are summarized in Table 2.

The experimental results reproduced in Table 2 show that methanesulfonic acid (MSA) is suitable in principle as a solvent in the oxidation of dimethyl disulfide (DMDS) to methanesulfonic acid. Depending on the selected reaction conditions (pressure, temperature and time), however, yields of methanesulfonic acid that differ sharply from one another are obtained. The methanesulfonic acid yield, for instance, fluctuates between 78.0% (experiment 1) and >99.0% (experiments 5, 6 and 10).

B) Productivity Optimization of the Reaction Parameters

In further experiments 11 to 22 in an autoclave, the reaction parameters were optimized with a view to maximum productivity (high methanesulfonic acid yield and low reaction time or residence time).

The individual compositions of reaction mixtures 11 to 22 and the specific reaction conditions in these experiments are summarized in Table 3. Depending on the particular reaction temperature, for ratios of dimethyl disulfide to nitric acid in the range from 100:1 (mol/mol) to 1:1 (mol/mol), virtually complete conversion of the dimethyl disulfide is obtained within just an hour. In experiment 21, indeed, complete conversion of the dialkyl disulfide is achieved within half an hour.

TABLE 2

Overview of experiments 1 to 10 on the suitability of MSA as solvent in the preparation of MSA from DMDS.

| | Reaction mixture | | | | | | | | |
|---|---|---|---|---|---|---|---|---|---|
| No. | MSA [wt.-%]/[mmol] | DMDS [wt.-%]/[mmol] | $H_2O$ [wt.-%]/[mmol] | $HNO_3$ (65%) [wt.-%]/[mmol] | MMTS [wt.-%]/[mmol] | p [bara] | T [° C.] | t [h] | Yield of MSA [%] |
| 1 | 88.0/2665.0 | 9.8/301 | 1.7/307 | 0.51/15.47 | — | 6 | 50 | 3 | 78.0 |
| 2 | 88.0/2665.0 | 9.8/301 | 1.7/307 | 0.51/15.47 | — | 6 | 60 | 3 | 88.5 |
| 3 | 82.3/2050.0 | 13.7/347 | 3.2/464 | 0.71/17.54 | — | 3 | 70 | 3 | 96.3 |
| 4 | 82.3/2050.0 | 13.7/347 | 3.2/464 | 0.71/17.54 | — | 6 | 70 | 3 | 97.6 |
| 5 | 82.3/2050.0 | 13.7/347 | 3.2/464 | 0.71/17.54 | — | 9 | 70 | 3 | >99.0 |
| 6 | 82.3/2050.0 | 13.7/347 | 3.2/464 | 0.71/17.54 | — | 12 | 70 | 3 | >99.0 |
| 7 | 82.5/2050.0 | 13.8/347 | 3.3/460 | 0.46/11.35 | — | 6 | 70 | 3 | 89.7 |
| 8 | 82.0/2050.0 | 13.8/347 | 3.0/463 | 1.41/35.07 | — | 6 | 70 | 3 | 90.6 |
| 9 | 87.7/2050.0 | 13.6/347 | 4.0/575 | 0.70/17.54 | — | 6 | 70 | 3 | 88.2 |
| 10 | 81.8/2050.0 | 6.8/174 | 1.6/250 | 0.70/17.54 | 9.0/174 | 6 | 70 | 3 | >99.0 |

TABLE 3

Productivity optimization of the reaction parameters ($^a$ MSA used as solvent, $^b$ total amount of MSA, inclusive of solvent)

| | Reaction mixture | | | | | | Reaction conditions | | | | Product | | |
|---|---|---|---|---|---|---|---|---|---|---|---|---|---|
| No. | $MSA^a$ [g]/[wt.-%] | DMDS [g]/ [wt.-%] | $HNO_3$ (65%) [g]/[wt.-%] | $H_2O$ [wt.-%] | MSA/ DMDS [mol/mol] | DMDS/ $HNO_3$ [mol/mol] | $O_2$ [g] | p [bara] | T [° C.] | t [min] | $MSA^b$ [wt.-%] | DMDS [wt.-%] | MMTS [wt.-%] |
| 11a | 201.1/92.9 | 13.07/6.0 | 0.22/0.0020 | 1.146 | 15.2 | 2000 | 1.8 | 6 | 70 | 15 | 92.5 | 3.1 | 1.3 |
| 11b | 201.1/92.9 | 13.07/6.0 | 0.22/0.0020 | 1.146 | 15.2 | 2000 | 3.4 | 6 | 70 | 45 | 92.6 | 3.0 | 1.8 |
| 11c | 201.1/92.9 | 13.07/6.0 | 0.22/0.0020 | 1.146 | 15.2 | 2000 | 4.1 | 6 | 70 | 95 | 93.3 | 2.6 | 1.3 |
| 11d | 201.1/92.9 | 13.07/6.0 | 0.22/0.0020 | 1.146 | 15.2 | 2000 | 4.4 | 6 | 70 | 280 | 94.3 | 1.0 | 0.2 |
| 12a | 201.1/92.9 | 13.07/6.0 | 0.0040 | 1.145 | 15.2 | 1000 | 1.5 | 6 | 70 | 10 | 93.3 | 3.4 | 1.5 |
| 12b | 201.1/92.9 | 13.07/6.0 | 0.0040 | 1.145 | 15.2 | 1000 | 2.6 | 6 | 70 | 20 | 93.4 | 3.0 | 1.6 |
| 12c | 201.1/92.9 | 13.07/6.0 | 0.0040 | 1.145 | 15.2 | 1000 | 3.0 | 6 | 70 | 30 | 93.5 | 2.7 | 1.6 |
| 12d | 201.1/92.9 | 13.07/6.0 | 0.0040 | 1.145 | 15.2 | 1000 | 3.5 | 6 | 70 | 60 | 93.9 | 2.4 | 1.4 |
| 12e | 201.1/92.9 | 13.07/6.0 | 0.0040 | 1.145 | 15.2 | 1000 | 3.9 | 6 | 70 | 120 | 94.4 | 2.0 | 0.8 |
| 12f | 201.1/92.9 | 13.07/6.0 | 0.0040 | 1.145 | 15.2 | 1000 | 4.2 | 6 | 70 | 194 | 94.5 | 1.7 | 0.5 |
| 13a | 201.1/92.8 | 13.07/6.0 | 0.0080 | 1.143 | 15.2 | 500 | 4.3 | 6 | 70 | 15 | 93.9 | 1.1 | 0.3 |
| 13b | 201.1/92.8 | 13.07/6.0 | 0.0080 | 1.143 | 15.2 | 500 | 7.7 | 6 | 70 | 30 | 95.9 | 1.6 | 0.7 |
| 13c | 201.1/92.8 | 13.07/6.0 | 0.0080 | 1.143 | 15.2 | 500 | 9.3 | 6 | 70 | 45 | 97.5 | 0.7 | 0.4 |
| 13d | 201.1/92.8 | 13.07/6.0 | 0.0080 | 1.143 | 15.2 | 500 | 10.6 | 6 | 70 | 60 | 97.8 | 0.1 | 0.1 |
| 13e | 201.1/92.8 | 13.07/6.0 | 0.0080 | 1.143 | 15.2 | 500 | 11.1 | 6 | 70 | 90 | 98.6 | 0.0 | 0.05 |
| 14a | 201.1/92.8 | 13.07/6.0 | 0.0201 | 1.137 | 15.2 | 200 | 2.4 | 6 | 70 | 10 | 94.2 | 3.1 | 1.1 |
| 14b | 201.1/92.8 | 13.07/6.0 | 0.0201 | 1.137 | 15.2 | 200 | 4.0 | 6 | 70 | 15 | 94.5 | 2.5 | 1.0 |
| 14c | 201.1/92.8 | 13.07/6.0 | 0.0201 | 1.137 | 15.2 | 200 | 5.1 | 6 | 70 | 20 | 96.0 | 2.0 | 0.8 |
| 14d | 201.1/92.8 | 13.07/6.0 | 0.0201 | 1.137 | 15.2 | 200 | 7.1 | 6 | 70 | 30 | 96.9 | 1.1 | 0.5 |
| 14e | 201.1/92.8 | 13.07/6.0 | 0.0201 | 1.137 | 15.2 | 200 | 9.1 | 6 | 70 | 45 | 97.9 | 0.3 | 0.3 |
| 14f | 201.1/92.8 | 13.07/6.0 | 0.0201 | 1.137 | 15.2 | 200 | 10.2 | 6 | 70 | 60 | 98.5 | 0.0 | 0.05 |
| 15a | 201.1/92.8 | 13.07/6.0 | 0.0401 | 1.125 | 15.2 | 100 | 3.1 | 6 | 70 | 10 | 94.2 | 3.0 | 1.0 |
| 15b | 201.1/92.8 | 13.07/6.0 | 0.0401 | 1.125 | 15.2 | 100 | 4.5 | 6 | 70 | 15 | 95.1 | 2.4 | 0.8 |
| 15c | 201.1/92.8 | 13.07/6.0 | 0.0401 | 1.125 | 15.2 | 100 | 6.0 | 6 | 70 | 20 | 97.1 | 1.9 | 0.6 |
| 15d | 201.1/92.8 | 13.07/6.0 | 0.0401 | 1.125 | 15.2 | 100 | 8.1 | 6 | 70 | 30 | 97.7 | 0.8 | 0.3 |
| 15e | 201.1/92.8 | 13.07/6.0 | 0.0401 | 1.125 | 15.2 | 100 | 9.7 | 6 | 70 | 45 | 98.8 | 0.05 | 0.05 |
| 15f | 201.1/92.8 | 13.07/6.0 | 0.0401 | 1.125 | 15.2 | 100 | 10.2 | 6 | 70 | 60 | 99.8 | 0.01 | 0.01 |
| 16a | 201.1/92.8 | 13.07/6.0 | 0.0502 | 1.120 | 15.2 | 80 | 3.2 | 6 | 70 | 10 | 94.4 | 3.2 | 1.0 |

TABLE 3-continued

Productivity optimization of the reaction parameters ($^a$ MSA used as solvent, $^b$ total amount of MSA, inclusive of solvent)

| | Reaction mixture | | | | | | Reaction conditions | | | | Product | | |
|---|---|---|---|---|---|---|---|---|---|---|---|---|---|
| No. | MSA$^a$ [g]/[wt.-%] | DMDS [g]/[wt.-%] | HNO$_3$ (65%) [g]/[wt.-%] | H$_2$O [wt.-%] | MSA/ DMDS [mol/mol] | DMDS/ HNO$_3$ [mol/mol] | O$_2$ [g] | p [bara] | T [° C.] | t [min] | MSA$^b$ [wt.-%] | DMDS [wt.-%] | MMTS [wt.-%] |
| 16b | 201.1/92.8 | 13.07/6.0 | 0.0502 | 1.120 | 15.2 | 80 | 4.8 | 6 | 70 | 15 | 95.5 | 2.5 | 0.8 |
| 16c | 201.1/92.8 | 13.07/6.0 | 0.0502 | 1.120 | 15.2 | 80 | 6.2 | 6 | 70 | 20 | 96.0 | 1.7 | 0.6 |
| 16d | 201.1/92.8 | 13.07/6.0 | 0.0502 | 1.120 | 15.2 | 80 | 8.6 | 6 | 70 | 30 | 97.3 | 0.7 | 0.3 |
| 16e | 201.1/92.8 | 13.07/6.0 | 0.0502 | 1.120 | 15.2 | 80 | 10.5 | 6 | 70 | 45 | 98.7 | 0.05 | 0.05 |
| 17a | 201.1/92.8 | 13.07/6.0 | 0.0669 | 1.111 | 15.2 | 60 | 4.8 | 6 | 70 | 10 | 95.1 | 2.5 | 0.8 |
| 17b | 201.1/92.8 | 13.07/6.0 | 0.0669 | 1.111 | 15.2 | 60 | 6.7 | 6 | 70 | 15 | 96.3 | 1.7 | 0.5 |
| 17c | 201.1/92.8 | 13.07/6.0 | 0.0669 | 1.111 | 15.2 | 60 | 8.2 | 6 | 70 | 20 | 97.6 | 0.9 | 0.4 |
| 17d | 201.1/92.8 | 13.07/6.0 | 0.0669 | 1.111 | 15.2 | 60 | 10 | 6 | 70 | 30 | 98.5 | 0.1 | 0.1 |
| 17e | 201.1/92.8 | 13.07/6.0 | 0.0669 | 1.111 | 15.2 | 60 | 10.6 | 6 | 70 | 45 | 98.7 | 0.05 | 0.05 |
| 18a | 201.1/92.8 | 13.07/6.0 | 0.143 | 1.1 | 15.2 | 40 | 3.3 | 6 | 70 | 10 | 94.3 | 3.1 | 0.9 |
| 18b | 201.1/92.8 | 13.07/6.0 | 0.143 | 1.1 | 15.2 | 40 | 4.6 | 6 | 70 | 15 | 95.1 | 2.4 | 0.7 |
| 18c | 201.1/92.8 | 13.07/6.0 | 0.143 | 1.1 | 15.2 | 40 | 6.2 | 6 | 70 | 20 | 96.6 | 1.7 | 0.5 |
| 18d | 201.1/92.8 | 13.07/6.0 | 0.143 | 1.1 | 15.2 | 40 | 7.5 | 6 | 70 | 25 | 97.6 | 1.1 | 0.3 |
| 18e | 201.1/92.8 | 13.07/6.0 | 0.143 | 1.1 | 15.2 | 40 | 8.6 | 6 | 70 | 30 | 97.4 | 0.5 | 0.2 |
| 18f | 201.1/92.8 | 13.07/6.0 | 0.143 | 1.1 | 15.2 | 40 | 9.7 | 6 | 70 | 45 | 98.6 | 0 | 0 |
| 18g | 201.1/92.8 | 13.07/6.0 | 0.143 | 1.1 | 15.2 | 40 | 10.6 | 6 | 70 | 60 | 99.1 | 0 | 0 |
| 19a | 201.1/92.8 | 13.07/6.0 | 0.2 | 1.0 | 15.1 | 20 | 3.9 | 6 | 70 | 10 | 95.3 | 2.7 | 0.7 |
| 19b | 201.1/92.8 | 13.07/6.0 | 0.2 | 1.0 | 15.1 | 20 | 7.1 | 6 | 70 | 20 | 96.7 | 1.2 | 0.4 |
| 19c | 201.1/92.8 | 13.07/6.0 | 0.2 | 1.0 | 15.1 | 20 | 8.4 | 6 | 70 | 30 | 98.4 | 0.1 | 0.1 |
| 19d | 201.1/92.8 | 13.07/6.0 | 0.2 | 1.0 | 15.1 | 20 | 10.6 | 6 | 70 | 50 | 99.1 | 0 | 0 |
| 20a | 201.1/92.7 | 13.07/6.0 | 0.4022 | 0.9313 | 15.1 | 10 | 5.2 | 6 | 70 | 10 | 95.0 | 2.4 | 0.6 |
| 20b | 201.1/92.7 | 13.07/6.0 | 0.4022 | 0.9313 | 15.1 | 10 | 7.0 | 6 | 70 | 15 | 97.2 | 1.3 | 0.4 |
| 20c | 201.1/92.7 | 13.07/6.0 | 0.4022 | 0.9313 | 15.1 | 10 | 9.3 | 6 | 70 | 20 | 97.8 | 0.5 | 0.2 |
| 20d | 201.1/92.7 | 13.07/6.0 | 0.4022 | 0.9313 | 15.1 | 10 | 10.9 | 6 | 70 | 30 | 98.4 | 0 | 0.0 |
| 21a | 201.1/91.8 | 13.07/6.0 | 2.029 | 0.0669 | 14.8 | 2 | 2.4 | 6 | 70 | 10 | 95.7 | 2.3 | 0.8 |
| 21b | 201.1/91.8 | 13.07/6.0 | 2.029 | 0.0669 | 14.8 | 2 | 4.9 | 6 | 70 | 15 | 97.6 | 1.6 | 0.6 |
| 21c | 201.1/91.8 | 13.07/6.0 | 2.029 | 0.0669 | 14.8 | 2 | 6.7 | 6 | 70 | 20 | 97.9 | 1.0 | 0.3 |
| 21d | 201.1/91.8 | 13.07/6.0 | 2.029 | 0.0669 | 14.8 | 2 | 10.3 | 6 | 70 | 30 | 98.0 | 0.0 | 0.0 |
| 22a | 201.1/90.8 | 13.07/6.0 | 4.102 | 0 | 14.5 | 1 | 6.4 | 6 | 70 | 10 | 96.4 | 0.6 | 0.3 |
| 22b | 201.1/90.8 | 13.07/6.0 | 4.102 | 0 | 14.5 | 1 | 10.0 | 6 | 70 | 15 | 96.4 | 0 | 0 |

C) Safety Optimization of the Reaction Parameters

In experiments 23 to 27, the reaction behaviour of different mixtures of dimethyl disulfide, methanesulfonic acid, nitric acid and water was examined from the standpoint of plant safety, with addition of pure oxygen under largely adiabatic conditions. For this purpose, a number of experiments were conducted with different experimental conditions, using in each case a closed sample in an adiabatic calorimeter (Phitec II).

1. Samples
  1.1 Methanesulfonic Acid
  1.2 Dimethyl Disulfide
  1.3 Nitric Acid, 65% Strength
  1.4 DI Water (Deionized Water, i.e. Fully Demineralized Water)
2. Investigation of Reaction Behaviour Under Adiabatic Conditions
  2.1 Measurements in the Adiabatic Calorimeter (Phi-TEC II)
    2.1.1 Measurement Method The Phi-TEC II is a PC-controlled calorimeter which can be used to simulate the behaviour of a large reactor under conditions of an industrial plant even using relatively small quantities of sample, such as 10 to 100 ml, for example.

With the PHITEC II calorimeter, a pressure/heat accumulation method is employed in which (depending on the mandated experimental conditions) a relatively high measurement accuracy is obtained, taking account of the detectable heat output in the reaction (typically about 2-5 W/kg when using a closed sample container). From the profile of the temperature and of the pressure, measured over time, reflecting the exothermicity of the reaction and the formation of decomposition gases, the thermal stability of the sample in question can be investigated.

The experiments are carried out using an adiabatic calorimeter; the entire measurement apparatus is installed in a pressure-resistant autoclave.

Inserted into the pressure vessel is a cylindrical sample container made from stainless steel of material number 1.457 (alternatively, a sample container made of Hastelloy) with a volume of 110 ml, insertion taking place into a heater system whose heating units, while fully surrounding the sample container, do not have any mechanical contact with it. Using a magnetic stirring rod (also referred to as magnetic flea or stirring bar), which is located on the base of the sample vessel, the sample is stirred.

The sample container has very thin walls, with a wall thickness of typically only 0.15 mm. The pressure which comes about in the closed sample container in the course of a measurement, therefore, and which is composed of the vapour pressure and the partial pressure of decomposition gases, is also established, via a tracking control system, in the surrounding autoclave, in order to prevent deformation of the sample container.

The ambient temperature of the sample container is adapted continually to the sample temperature, thereby largely preventing a flow of heat from the sample into the ambient environment. The ambient temperature is therefore regulated in such a way that at no point in time is the difference between the sample temperature and the ambient temperature 0 Kelvin, and so adiabatic conditions prevail.

The favourable ratio of the heat capacity of the sample container to the heat capacity of the sample results in a relatively high sensitivity of measurement, which is quantified by the so-called phi factor φ, as given by the following equation:

$$\Phi = \frac{\text{Heat capacity of sample} + \text{heat capacity of sample container}}{\text{Heat capacity of sample}}$$

The value of the dimensionless phi factor is ideally not much more than 1.

The maximum adiabatic temperature increase determined in each experiment is corrected by the phi factor, in order to take account of the energy needed to heat the container.

2.1.2 Experimental Procedure and Measurement Results 2.1.2.1 Experiment 23

A closed sample container made from the nickel-chromium-molybdenum alloy Hastelloy C276 was used, with a volume of 115 ml, the container being equipped with an immersion tube for the feeding-in of molecular oxygen, and with a stirring bar.

The composition of the sample for the experiment is summarized in the table below:

|  | [g] | [%] | Density [g/ml] | [ml] | [g] | [%] | [ml] |
|---|---|---|---|---|---|---|---|
| Methanesulfonic acid | 198 | 74.24 | 1.48 | 133.78 | 79.2 | 74.24 | 53.51 |
| Nitric acid (65%) | 2.75 | 1.03 | 1 | 2.75 | 1.1 | 1.03 | 1.10 |
| Dimethyl disulfide | 53.45 | 20.04 | 1.03 | 51.89 | 21.38 | 20.04 | 20.76 |
| Water | 12.5 | 4.69 | 1 | 12.50 | 5 | 4.69 | 5.00 |
| Total: | 266.7 | 100.00 |  | 200.93 | 106.68 | 100.00 | 80.37 |

Under intrinsic vapour pressure, the sample container, which had been evacuated beforehand, was charged first with the methanesulfonic acid and also with the fractions of nitric acid and water, and then dimethyl disulfide was added. Thereafter the sample was heated to the setpoint temperature of 70° C. When the heater was switched off, a weakly exothermic reaction was apparent in the subsequent period, in which a temperature of 72° C. was reached up to the point of addition of the oxygen. This was followed by the addition of pure oxygen, with an initial pressure in the sample container of about 7.5 bara, with the objective of using the feeding-in of oxygen to set an overall pressure of 12 bara as rapidly as possible. For this purpose, the pressure reduction station of the oxygen flask was set to the target pressure and verified using a reference pressure manometer. A reverse flow preventer installed in the feed line prevented backward flow of the gas. Immediately after the introduction of the oxygen, a very strongly exothermic reaction began, in association with very rapid pressure rise.

Owing to the very strongly exothermic reaction, the pressure in the sample container, in spite of pressure limitation and shut-off of the feed-line valve for the oxygen, rose well beyond the setpoint pressure, and reached a maximum of 20.4 bara. The sample temperature reached a maximum of 119° C. Since the tracking control system of the temperature was unable to follow the very rapid temperature rise, it is assumed that the achievable temperature maximum would be even higher. (Not included in the appraisal of the temperature increase and pressure increase are the effects of the rate of introduction of the oxygen and of a fraction of heat of compression resulting from the injection.)

After the temperature and the pressure had dropped to about 84° C. and to about 11.2 bara, respectively, oxygen was injected again at up to 12 bara. This produced a further exothermic effect, although significantly weaker in extent by comparison with the first addition of oxygen.

FIGS. 1 and 2 show the time-dependent profiles of the sample temperature and of the pressure, respectively, and FIG. 3 shows the temperature-dependent profile of the pressure. The uncertainty of results is ±1 K for the temperature and ±0.4 bar for the pressure. FIG. 4 shows the time-dependent change in temperature as a function of the sample temperature, and FIG. 5 represents the temperature relationship of the heat output. For the calculation of the exothermic heat output, the specific heat of the sample was estimated at constant pressure ($c_p$) For this purpose, for the fraction of organic compounds, the assumption was made of a specific heat at constant pressure ($c_p$) of 2 J/(g*K), and a ($c_p$) of 4.1 J/(g*K) for the inorganic fraction.

Owing to the concentration of dimethyl disulfide, there was a very rapid increase in temperature and pressure when this experiment was carried out. Under the experimental conditions, however, there was no damage, and certainly not any destruction, of the sample container. The temperature and pressure increase that occurred in this experiment was therefore non-critical. The concentration of 20 wt.-% therefore represents the marginal region in the process of the invention at which the oxidation of the dialkyl disulfide to the corresponding alkanesulfonic acid can still be carried out safely and readily. For a controllable implementation of the oxidation of the dialkyl disulfide to the alkanesulfonic acid, therefore, the concentration of the dialkyl disulfide in the reaction mixture ought to be not more than 20 wt.-%, preferably less than 20 wt.-%.

2.1.2.2 Experiment 24

In this experiment, the reaction effluent from experiment 23 was used, and the effect of the addition of oxygen at different temperatures was investigated. For this purpose, the sample container was filled with the reaction effluent from experiment 23, and the sample was first heated to the setpoint temperature of 50° C. with the stirrer running. After the heater had been switched off, the pressure was about 0.7 bara and the temperature remained constant. Thereafter the pure oxygen was added via the immersion tube of the sample container, with the aim of achieving a final setpoint pressure of 12 bara. For this purpose, the pressure reduction station of the oxygen flask was set to this pressure and checked using a reference pressure manometer. A reverse flow preventer installed in the feed line prevented the gas from flowing back.

Even with a relatively quick injection of the oxygen, a rapid temperature rise was evident, initially up to about 60° C. At this point the pressure in the sample container, despite pressure limitation and shut-off of the oxygen feed-line valve, rose above the setpoint pressure and reached a value of about 13 bara. After a slight drop, the sample temperature rose without external supply of energy, solely as a result of the heat released during the exothermic reaction, up to about 105° C. This was paralleled by a drop in the pressure from 13 bara to 3 bara. After heating to 111° C. and a short run-in phase, oxygen was again injected to a setpoint pressure of 12 bara, with a pressure of 12.1 bara becoming established. Both during the injection and also thereafter, there was only a slight change in temperature observed, of about 1 K. This was followed by a further two heating steps to a final temperature of 121° C., but no exothermic reaction was observed. The experiment was therefore discontinued. After cooling to room temperature and release of pressure on the sample container, the remnant sample was removed.

FIG. 6 shows the time-dependent profile of the sample temperature, and FIGS. 7 and 8 show the time-dependent and temperature-dependent profiles of the pressure, respectively. The measurement accuracy is ±1 K for the temperature and ±0.4 bar for the pressure.

The profile of temperature and pressure as shown in FIGS. 6 and 7 indicates that in the subsequent reaction of the reaction effluent from experiment 23 there is still a certain conversion. In this subsequent reaction, however, both the development of temperature and the development of pressure are significantly lower than in the preceding conversion. The two experiments 23 and 24 show that the oxidation of dialkyl disulfide to the corresponding alkanesulfonic acid can be carried out controllably in two successive reactors.

2.1.2.3 Experiment 25

In this experiment, the oxygen was added at 50° C. (in contrast to the corresponding temperature of 70° C. in experiment 23) and the setpoint pressure was 12 bara. For this purpose, a closed sample container made from the stainless steel alloy Hastelloy C276 was used, with a volume of 115 ml, this container being equipped with an immersion tube and a stirring rod or stirring flea.

The composition of the sample for the experiment is as follows:

|  | [g] | [%] | Density [g/ml] | [ml] | [g] | [%] | [ml] |
|---|---|---|---|---|---|---|---|
| Methanesulfonic acid | 198 | 74.24 | 1.48 | 133.78 | 79.2 | 74.24 | 53.51 |
| Nitric acid (65%) | 2.75 | 1.03 | 1 | 2.75 | 1.1 | 1.03 | 1.10 |
| Dimethyl disulfide | 53.45 | 20.04 | 1.03 | 51.89 | 21.38 | 20.04 | 20.76 |
| Water | 12.5 | 4.69 | 1 | 12.50 | 5 | 4.69 | 5.00 |
| Total: | 266.7 | 100.00 |  | 200.93 | 106.68 | 100.00 | 80.37 |

Under intrinsic vapour pressure, the sample container, which had been evacuated beforehand, was charged first with the methanesulfonic acid and also with the corresponding fractions of nitric acid and water. Subsequently the corresponding fraction of dimethyl disulfide was added to the sample container. Thereafter the sample was heated to the setpoint temperature of 50° C., with the stirrer running.

When the heater was switched off, a very weakly exothermic reaction was apparent in the subsequent period, in which a temperature of 51.4° C. was reached up to the point of addition of the oxygen. At a pressure of about 6.7 bara, the addition of pure oxygen via the immersion tube in the sample container was commenced, in order to set a total pressure of 12 bara with the use of oxygen as rapidly as possible. For this purpose, the pressure reduction station of the oxygen flask was set to the corresponding pressure and verified using a reference pressure manometer. A reverse flow preventer installed in the feed line prevented backward flow of the gas stream. Immediately after the introduction of the oxygen, a very strongly exothermic reaction was apparent, in association with very rapid pressure rise. Despite pressure limitation on the oxygen supply flask and closing of the inlet valve, the pressure in the sample container rose to about 18.5 bara. The sample temperature reached a maximum of about 98° C. Since the tracking control system of the temperature was unable to follow the very rapid temperature rise, it is assumed that the achievable temperature maximum would be even higher. (Not included in the appraisal of the temperature increase and pressure increase are the effects of the rate of introduction of the oxygen and of a fraction of heat of compression resulting from the injection.) After the attainment of the temperature maximum and the shutting-off of the oxygen supply, and also a drop in pressure to about 8.9 bara, the experiment was ended.

FIG. 9 shows the time-dependent profile of the sample temperature. FIGS. 10 and 11 represent the time-dependent and temperature-dependent profile of the pressure, respectively. The measurement accuracy is ±1 K for the temperature and ±0.4 bar for the pressure. FIG. 12 shows the time-dependent change in temperature as a function of the sample temperature, and FIG. 13 shows the heat output as a function of the sample temperature. For the calculation of the (exothermic) heat output, the specific heat of the sample at constant pressure ($c_p$) is estimated. For this purpose, for the fraction of organic compounds, a specific heat at constant pressure ($c_p$) of 2 J/(g*K) is assumed, and a ($c_p$) of 4.1 J/(g*K) for the inorganic fraction.

In experiment 25, the oxidation of the dimethyl disulfide to the corresponding methanesulfonic acid is initiated by feeding in oxygen at a temperature of 50° C., which is 20° C. lower than the corresponding temperature in experiment 23. Accordingly, the curve profiles for the time-dependent change in temperature and for the heat output of the reaction are also shifted by this temperature difference in experiment 25 by comparison with the corresponding curve profiles in experiment 23. Apart from this shift, the profile for the time-dependent change in temperature and the profile for the heat output in experiment 25 are parallel to those in experiment 23 (cf. FIGS. 4 to 5 and 12 to 13). Similar comments also apply in respect of the development of temperature and of pressure in experiments 23 and 25 (cf. FIGS. 1 to 2 and 9 to 11).

The results of experiments 23 and 25 show that the oxidation of the dialkyl disulfide proceeds with a comparable exotherm in both experiments, independently of the respective starting temperature.

2.1.2.4 Experiment 26

In contrast to experiments 23 to 25, which used a sample container made from the Hastelloy C276 alloy, and with an immersion tube, this experiment was conducted in a sample container made from a stainless steel with material number 1.4571. The closed sample container in this experiment has a volume of 110 ml and is equipped with a stirring bar or stirring flea, but not with an immersion tube.

The initial setpoint temperature before the addition of oxygen was 50° C., and the setpoint pressure for the addition of oxygen was 12 bara.

The composition of the sample for the experiment is summarized in the table below:

|  | [g] | [%] | Density [g/ml] | [ml] | [g] | [%] | [ml] |
|---|---|---|---|---|---|---|---|
| Methanesulfonic acid | 198 | 74.24 | 1.48 | 133.78 | 79.2 | 74.24 | 53.51 |
| Nitric acid (65%) | 2.75 | 1.03 | 1 | 2.75 | 1.1 | 1.03 | 1.10 |
| Dimethyl disulfide | 53.45 | 20.04 | 1.03 | 51.89 | 21.38 | 20.04 | 20.76 |
| Water | 12.5 | 4.69 | 1 | 12.50 | 5 | 4.69 | 5.00 |
| Total: | 266.7 | 100.00 |  | 200.93 | 106.68 | 100.00 | 80.37 |

Under intrinsic vapour pressure, the sample container, which had been evacuated beforehand, was charged first of all with the methanesulfonic acid and with the fractions of nitric acid and water. Thereafter the fraction of dimethyl disulfide was added to the sample container, followed by the heating of the sample to the setpoint temperature of 50° C., with the stirrer running.

The time-dependent profiles of the sample temperature (unbroken line) and of the pressure (broken line) are depicted jointly in FIG. 14. FIG. 15 shows the time-dependent change in the sample temperature as a function of the sample temperature, and FIG. 16 the temperature-dependent pressure profile.

After the heater was switched off when the setpoint temperature of 50° C. was reached, a temperature of about 51.5° C. was established in the subsequent period, before commencement of addition of oxygen. This was followed by addition of pure oxygen at a pressure in the sample container of about 71.2 bara, with the objective of setting an overall pressure of 12 bara as rapidly as possible by the feeding-in of oxygen. For this purpose the pressure reduction station of the oxygen flask was set to the target pressure, and checked using a reference pressure manometer. A reverse flow preventer installed in the feed line prevented the gas from flowing back. With a certain delay, there was a very strongly exothermic reaction after the introduction of the oxygen, and a temperature maximum of about 350° C. was reached. The delay is attributed to the fact that in contrast to experiments 23 to 25, oxygen is not introduced into the sample container via an immersion tube, but instead is introduced from above onto the liquid phase.

In the phase of the addition of the oxygen, a banging noise was heard from the autoclave box in which the calorimeter had been placed for the experiments. The experiment was subsequently ended by switching off the heating system. A real pressure increase of up to about 5.5 bara was still recorded, but the subsequent pressure/time profile was no longer recorded. This is attributable to the destruction of the pressure transducer, whose maximum permissible pressure is 100 bar.

The vapours of dimethyl disulfide are able, with air or oxygen, to form an explosive mixture; the corresponding ignition temperature is 370° C. With regard to the ignition temperature of mixtures of flammable gases and vapours with air or oxidizing gas, it is known that the temperature decreases very sharply with increasing pressure (cf. e.g. Hirsch, W., Brandes, E., "Zündtemperaturen binärer Gemische bei erhöhten Ausgangsdrücken", Physikalisch Technische Bundesanstalt, Braunschweig, 2005). With the sharp increase in the temperature and the increased initial pressure on addition of oxygen, the preconditions for the obtainment of the ignition temperature were provided for dimethyl disulfide. Despite the free gas volume in the sample container being relatively small, it can therefore very probably be assumed that there was self-ignition of the gas phase containing oxygen and dimethyl disulfide.

This experiment clearly shows that the formation of explosion hazard mixtures from ignitable dialkyl disulfides with oxygen must fundamentally be avoided.

2.1.2.5 Experiment 27

A sample container made from the alloy Hastelloy C276 was used. This closed sample container has a volume of 115 ml and is equipped with an immersion tube and with a stirring bar or stirring flea.

The initial setpoint temperature before the addition of oxygen was 50° C., and the setpoint pressure for the addition of oxygen was 12 bara.

The composition of the sample for the experiment is summarized in the table below:

|  | [g] | [%] | Density [g/ml] | [ml] | [g] | [%] | [ml] |
|---|---|---|---|---|---|---|---|
| Methanesulfonic acid | 302 | 87.66 | 1.48 | 204.05 | 100.67 | 87.67 | 68.02 |
| Nitric acid (65%) | 1.7 | 0.49 | 1 | 1.70 | 0.57 | 0.49 | 0.57 |
| Dimethyl disulfide | 33 | 9.58 | 1.03 | 32.04 | 11.00 | 9.58 | 10.68 |
| Water | 7.8 | 2.26 | 1 | 7.80 | 2.60 | 2.26 | 2.60 |
| Total: | 344.5 | 100.00 |  | 245.59 | 114.83 | 100.00 | 81.86 |

Under intrinsic vapour pressure, the sample container, which had been evacuated beforehand, was charged first of all with the methanesulfonic acid and with the fractions of nitric acid and water. Thereafter the fraction of dimethyl disulfide was added to the sample container, followed by the heating of the sample to the setpoint temperature of 70° C., with the stirrer running.

The time-dependent profile of sample temperature and pressure is depicted in FIGS. 17 and 18, respectively. FIG. 19 shows the temperature-dependent pressure profile, and FIG. 20 shows the time-dependent change in the sample temperature as a function of the sample temperature.

An exothermic reaction started immediately after the heater was switched off, when a temperature of 70° C. was reached. At about 71.3° C., oxygen was added rapidly with the aim of establishing a pressure of 12 bara. When this pressure had been reached and the inlet valve was closed for the first time, the sample temperature was about 93° C.

Following the subsequent drop in pressure, oxygen was injected repeatedly in order to re-establish a pressure of 12 bara. The accompanying increase in temperature, however, was no longer spontaneous, but instead was relatively slow. Over a time of approximately 4900 seconds, with repeated further addition of oxygen, a maximum sample temperature of about 110° C. was attained.

In this experiment, not only the development of temperature but also the development of pressure are much smaller than in experiments 23 and 25 (cf. FIGS. 17 and 18). In contrast to experiments 23 and 25, therefore, the starting concentration selected for the dimethyl disulfide in this experiment permits discontinuous addition of oxygen over a prolonged time period, without the setpoint pressure of 12 bara being markedly exceeded. The process parameters of experiment 27, especially the selected concentration of the dimethyl disulfide, therefore permit a corresponding process for the preparation of methanesulfonic acid to be operated with no safety problems.

The invention claimed is:

1. A process for preparing an alkanesulfonic acid of the formula R—SO$_3$—H, comprising:
   oxidizing a symmetrical dialkyl disulfide of the formula R—S$_2$—R, in solution in an alkanesulfonic acid, in the presence of a catalytic amount of nitric acid, with R denoting a C$_1$-C$_{12}$ alkyl radical and the alkanesulfonic acid used as solvent being identical with the alkanesulfonic acid obtained from the oxidation of the dialkyl disulfide,
   wherein the concentration of the dialkyl disulfide in the solution is not more than 20 weight percent, the ratio of dialkyl disulfide to nitric acid ranges from 2000:1 (mol/mol) to 1:1 (mol/mol), and the concentration of the alkanesulfonic acid used as solvent is more than 70 weight percent.

2. The process according to claim 1, wherein the dialkyl disulfide is dimethyl disulfide and the alkanesulfonic acid is methanesulfonic acid.

3. The process according to claim 1, wherein the ratio of dialkyl disulfide to nitric acid ranges from 500:1 (mol/mol) to 1:1 (mol/mol).

4. The process according to claim 1, wherein the ratio of dialkyl disulfide to nitric acid ranges from 500:1 (mol/mol) to 2:1 (mol/mol).

5. The process according to claim 1, wherein the concentration of the dialkyl disulfide in the alkanesulfonic acid is up to about 10 weight percent.

6. The process according to claim 1, wherein the process is carried out at temperatures of not more than about 90° C.

7. The process according to claim 6, wherein the process is carried out at temperatures of about 70° C. to about 90° C.

8. The process according to claim 1, wherein the concentration of the alkanesulfonic acid used as solvent is at least 80 weight percent.

9. The process according to claim 8, wherein the concentration of the alkanesulfonic acid used as solvent is at least about 90 weight percent.

10. The process according to claim 1, wherein, for the oxidation, air, a gas stream enriched with oxygen in free form, and/or pure oxygen in free form is fed in.

11. The process according to claim 10, wherein, for the oxidation, a gas stream comprising oxygen, containing more than 21 vol.-% of oxygen in free form, is fed in.

12. The process according to claim 1, wherein the process is carried out at a pressure of more than 1 bara to about 20 bara.

13. The process according to claim 12, wherein the process is carried out at a pressure of more than 2 bara to about 15 bara.

14. The process according to claim 1, wherein a solubilizer between the dialkyl disulfide and the alkanesulfonic acid is used.

15. The process according to claim 14, wherein alkanesulfonic acid S-alkyl ester of the formula R—SO$_2$—S—R is used as solubilizer between the dialkyl disulfide and the alkanesulfonic acid, with the alkyl radicals of the alkanesulfonic acid S-alkyl ester being identical with the alkyl radicals of the dialkyl disulfide to be converted and with the alkyl radical of the alkanesulfonic acid.

16. A process for preparing an alkanesulfonic acid of the formula R—SO$_3$—H, comprising:
   oxidizing a symmetrical dialkyl disulfide of the formula R—S$_2$—R, in solution in an alkanesulfonic acid, in the presence of a catalytic amount of nitric acid, with R denoting a C$_1$-C$_{12}$ alkyl radical and the alkanesulfonic acid used as solvent being identical with the alkanesulfonic acid obtained from the oxidation of the dialkyl disulfide,
   wherein the concentration of the dialkyl disulfide in the solution is not more than 20 weight percent, the ratio of dialkyl disulfide to nitric acid ranges from 2000:1 (mol/mol) to 1:1 (mol/mol), and the concentration of the alkanesulfonic acid used as solvent is more than 70 weight percent;
   wherein a solubilizer between the dialkyl disulfide and the alkanesulfonic acid is used;
   wherein alkanesulfonic acid S-alkyl ester of the formula R—SO$_2$—S—R is used as solubilizer between the dialkyl disulfide and the alkanesulfonic acid, with the alkyl radicals of the alkanesulfonic acid S-alkyl ester being identical with the alkyl radicals of the dialkyl disulfide to be converted and with the alkyl radical of the alkanesulfonic acid.

* * * * *